(12) United States Patent
Latham et al.

(10) Patent No.: US 11,214,829 B2
(45) Date of Patent: Jan. 4, 2022

(54) METHODS, COMPOSITIONS, KITS, AND USES FOR ANALYSIS OF NUCLEIC ACIDS COMPRISING REPEATING A/T-RICH SEGMENTS

(71) Applicant: Asuragen, Inc., Austin, TX (US)

(72) Inventors: Gary J. Latham, Austin, TX (US); Sachin Sah, Cedar Park, TX (US)

(73) Assignee: ASURAGEN, INC., Austin, TX (US)

( * ) Notice: Subject to any disclaimer, the term of this patent is extended or adjusted under 35 U.S.C. 154(b) by 851 days.

(21) Appl. No.: 15/744,149

(22) PCT Filed: Jul. 22, 2016

(86) PCT No.: PCT/US2016/043503
§ 371 (c)(1),
(2) Date: Sep. 26, 2018

(87) PCT Pub. No.: WO2017/015543
PCT Pub. Date: Jan. 26, 2017

(65) Prior Publication Data
US 2018/0201985 A1    Jul. 19, 2018

Related U.S. Application Data

(60) Provisional application No. 62/196,239, filed on Jul. 23, 2015.

(51) Int. Cl.
*C12Q 1/68* (2018.01)
*C12Q 1/6844* (2018.01)

(52) U.S. Cl.
CPC ................... *C12Q 1/6844* (2013.01)

(58) Field of Classification Search
CPC .................................................. C12Q 1/6844
See application file for complete search history.

(56) References Cited

U.S. PATENT DOCUMENTS

| | | | |
|---|---|---|---|
| 4,683,202 A | 7/1987 | Mullis | |
| 5,188,934 A | 2/1993 | Menchen et al. | |
| 5,366,860 A | 11/1994 | Bergot et al. | |
| 5,648,211 A | 7/1997 | Fraiser et al. | |
| 5,750,341 A | 5/1998 | Macevicz | |
| 5,800,996 A | 9/1998 | Lee et al. | |
| 5,847,162 A | 12/1998 | Lee et al. | |
| 5,863,727 A | 1/1999 | Lee et al. | |
| 5,936,087 A | 8/1999 | Benson et al. | |
| 5,945,526 A | 8/1999 | Lee et al. | |
| 6,008,379 A | 12/1999 | Benson et al. | |
| 6,020,481 A | 2/2000 | Benson et al. | |
| 6,051,719 A | 4/2000 | Benson et al. | |
| 6,140,054 A | 10/2000 | Wittwer et al. | |
| 6,140,500 A | 10/2000 | Yan et al. | |
| 6,191,278 B1 | 2/2001 | Lee et al. | |
| 6,287,824 B1 | 9/2001 | Lizardi | |
| 6,306,597 B1 | 10/2001 | Macevicz | |
| 6,326,173 B1 | 12/2001 | Edman et al. | |
| 6,410,278 B1 | 6/2002 | Notomi et al. | |
| 7,115,400 B1 | 10/2006 | Adessi et al. | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,948,015 B2 | 5/2011 | Rothberg et al. | |
| 8,679,757 B2* | 3/2014 | Latham | C12Q 1/6858 435/6.12 |
| 8,815,508 B2 | 8/2014 | Roses | |
| 8,846,315 B2 | 9/2014 | Roses | |
| 9,102,666 B2 | 8/2015 | Roses et al. | |
| 2008/0160580 A1 | 7/2008 | Adessi et al. | |
| 2015/0073022 A1 | 3/2015 | Roses | |

(Continued)

FOREIGN PATENT DOCUMENTS

| | | |
|---|---|---|
| EP | 2 324 126 B1 | 4/2014 |
| EP | 2 789 695 A1 | 10/2014 |
| EP | 3 106 165 A1 | 12/2016 |

(Continued)

OTHER PUBLICATIONS

Fazekas, A.J., Steeves, R. and Newmaster, S.G., 2010. Improving sequencing quality from PCR products containing long mononucleotide repeats. Biotechniques, 48(4), pp. 277-285. (Year: 2010).*

Duenas, J.C.R., Panzetta-Dutari, G.M. and Gardenal, C.N., 1999. Specific requirements for PCR amplification of long mitochondrial A+ T-rich DNA. Biotechniques, 27(2), pp. 258-260. (Year: 1999).*

Oto, M., Koguchi, A. and Yuasa, Y., 1997. Analysis of a polyadenine tract of the transforming growth factor-β type II receptor gene in colorectal cancers by non-gel-sieving capillary electrophoresis. Clinical chemistry, 43(5), pp. 759-763. (Year: 1997).*

Cruchaga C, Nowotny P, Kauwe JS, et al. Alzheimer's Disease Neuroimaging Initiative Association and expression analyses with single-nucleotide polymorphisms in TOMM40 in Alzheimer disease. Arch Neurol. 2011, 68(8):1013-1019. (Year: 2011).*

Chen et al. 2010, An information-rich CGG repeat primed PCR that detects the full range of fragile X expanded alleles and minimizes the need for southern blot analysis. The Journal of Molecular Diagnostics 12(5):589-600. (Year: 2010).*

(Continued)

*Primary Examiner* — Teresa E Strzelecka
*Assistant Examiner* — Olayinka A Oyeyemi
(74) *Attorney, Agent, or Firm* — Finnegan, Henderson, Farabow, Garrett & Dunner LLP

(57) ABSTRACT

Described herein are methods, compositions, kits, and uses thereof for analysis of nucleic acid segments comprising a repeating A/T-rich segment, wherein the repeating A/T-rich segment is: (i) a homopolymeric segment comprising at least 10 A residues, at least 10 T residues, or at least 10 U residues, wherein the at least 10 A, T, or U residues are consecutive or interrupted once by one to three other nucleotides; or (ii) a segment comprising $(T_nA)_m$, $(AT_n)_m$, $(TA_n)_m$, or $(A_nT)_m$, wherein n is 2 or greater and m is such that the length of the repeating A/T-rich segment is 10 or more residues.

35 Claims, 20 Drawing Sheets

Specification includes a Sequence Listing.

(56) References Cited

U.S. PATENT DOCUMENTS

| | | |
|---|---|---|
| 2015/0073025 A1 | 3/2015 | Roses |
| 2016/0000769 A1 | 1/2016 | Roses et al. |

FOREIGN PATENT DOCUMENTS

| | | |
|---|---|---|
| WO | WO 97/45539 A1 | 12/1997 |
| WO | WO 2009/098298 A1 | 8/2009 |

OTHER PUBLICATIONS

Chen et al. 2011. High resolution methylation PCR for fragile X analysis: evidence for novel FMR1 methylation patterns undetected in southern blot analyses. Genetics in medicine: official journal of the American College of Medical Genetics 13(6): 528-538. (Year: 2011).*

Hantash et al., 2010. Qualitative assessment of FMR1 (CGG) n triplet repeat status in normal, intermediate, premutation, full mutation, and mosaic carriers in both sexes: implications for fragile X syndrome carrier and newborn screening. Genetics in Medicine, 12(3), pp. 162-173. (Year: 2010).*

Bernardi et al., 2013. Role of TOMM40 rs10524523 polymorphism in onset of Alzheimer's disease caused by the PSEN1 M146L mutation. Journal of Alzheimer's Disease, 37(2), pp. 285-289. (Year: 2013).*

Maruszak et al., 2012. TOMM40 rs10524523 polymorphism's role in late-onset Alzheimer's disease and in longevity. Journal of Alzheimer's Disease, 28(2), pp. 309-322. (Year: 2012).*

Li, G., Bekris, L.M., Leong, L., Steinhart, E.J., Shofer, J.B., Crane, P.K., Larson, E.B., Peskind, E.R., Bird, T.D. and Yu, C.E., 2013. TOMM40 intron 6 poly-T length, age at onset, and neuropathology of AD in individuals with APOE ε3/ε3. Alzheimer's & Dementia, 9 (5), pp. 554-561. (Year: 2013).*

Tassone, F., Pan, R., Amiri, K., Taylor, A.K. and Hagerman, P.J., 2008. A rapid polymerase chain reaction-based screening method for identification of all expanded alleles of the fragile X (FMR1) gene in newborn and high-risk populations. The Journal of Molecular Diagnostics, 10(1), pp. 43-49. (Year: 2008).*

Hixson, J.E. and Vernier, D.T., 1990. Restriction isotyping of human apolipoprotein E by gene amplification and cleavage with HhaI. Journal of lipid research, 31(3), pp. 545-548. (Year: 1990).*

Genbank Accession No. NG_042854—Homo sapiens translocase of outer mitochondrial membrane 40 (TOMM40), RefSeqGene on chromosome 19; nuclear gene for mitochondrial product (submitted Aug. 2015) from http://www.ncbi.nlm.nih.gov/nuccore/NG_042854). (Year: 2015).*

International Patent Application No. PCT/US2016/043503, filed Jul. 22, 2016, by Asuragen, Inc.: International Search Report and Written Opinion, dated Nov. 17, 2016 (12 pages).

Deiman, B. et al. (2008) "Efficient amplification with NASBA of hepatitis B virus, herpes simplex virus and methicillin resistant *Staphylococcus aureus* DNA" *J Virol Meth*, 151(2):283-293.

Fazekas, A.J. et al. (2010) "Improving sequencing quality from PCR products containing long mononucleotide repeats" *BioTechniques*, 48:277-285.

Fazekas, A.J. et al. (2010) "Stopping the stutter: Improvements in sequence quality from regions with mononucleotide repeats can increase the usefulness of non-coding regions for DNA barcoding" *Taxon*, 59(3):694-697.

Filipovic-Sadic, S. et al., (2010) "A Novel FMR1 PCR Method for the Routine Detection of Low Abundance Expanded Alleles and Full Mutations in Fragile X Syndrome" *Clin Chem*, 56(3):399-408; doi:10.1373/clinchem.2009.136101, Epub Jan. 7, 2010.

Flores-Renteria, L. et al. (2011) "A new approach to Improve the scoring of mononucleotide microsatellite loci" *American Journal of Botany*, e51-e53; doi:10.3732/ajb.1000428.

Gudmundsson, J. et al. (2009) "Genome-wide association and replication studies identify four variants associated with prostate cancer susceptibility" *Nat Genet*, 41:1122-1126.

Henke, W. et al. (1997) "Betaine improves the PCR amplification of GC-rich DNA sequences" *Nucl Acids Res*, 25(19):3957-3958.

Oto, M. et al. (1997) "Analysis of a polyadenine tract of the transforming growth factor-β type II receptor gene in colorectal cancers by non-gel-sieving capilary electrophoresis" *Clin Chem*, 43(5):759-763.

Out, A.A. et al. (2009) "Deep sequencing to reveal new variants in pooled DNA samples" *Hum Mutat*, 30(12):1703-1712.

Rondan Dueñas, J.C. et al. (1999) "Specific Requirements for PCR Amplification of Long Mitochondrial A+T-Rich DNA" 27:258-260.

Roses, A.D. et al. (2010) "A TOMM40 variable-length polymorphism predicts the age of late-onset Alzheimer's disease" *Pharmacogenomics J*, 10:375-384.

Roses, A.D. et al. (2013) "TOMM40 and APOE: Requirements for replication studies of association with age of disease onset and enrichment of a clinical trial" *Alzheimer's & Dementia*, 9:132-136.

Shinde, D. et al. (2003) "Taq DNA polymerase slippage mutation rates measured by PCR and quasi-likelihood analysis: (CA/GT)$_n$ and (A/T)$_n$ microsatellites" *Nucl Acids Res*, 31(3):974-980.

Turner, E.H. et al. (2009) "Massively parallel exon capture and library-free resequencing across 16 genomes" *Nat Methods*, 6:315-316. NIH Public Access Author Manuscript; available in PMC Nov. 1, 2009 (5 pages).

Statt, S. et al. (Nov. 11, 2016). "A Streamlined PCR Assay for Rapid and Accurate Genotyping of Poly-T Length Polymorphisms at RS10524523 of the TOMM40 Gene" (Poster Presentation) Association for Molecular Pathology (AMP) Conference.

Statt, S. et al. (Jul. 19, 2017). "Multi-site Evaluation of the AmplideX® PCR/CE TOMM40 Kit (RUO) for Rapid and Accurate Genotyping of Poly-T Length Polymorphisms at rs10524523 of the TOMM40 Gene" (Poster Presentation) Alzheimer's Association International Conference (AAIC).

Hall et al. (Jul. 16, 2017). "A Streamlined PCR-based Fragment Analysis Assay that Resolves Both Single Nucleotide and Poly-T Length Polymorphisms at APOE and TOMM40 Susceptibility Loci in Alzheimer's Disease" (Poster Presentation) Alzheimer's Association International Conference (AAIC).

Lutz et al. (Dec. 7, 2020). "A genetic enrichment strategy for delay of onset of Alzheimer's disease clinical trials" *Alzheimer's Dement.* 2020;16(Suppl. 5):e044920. https://doi.org/10.1002/alz.044920.

Lutz et al. (Jul. 2020). "A genetic enrichment strategy for delay of onset of Alzheimer's disease clinical trials" (Poster Presentation) Alzheimer's Association International Conference (AAIC).

* cited by examiner

METHODS, COMPOSITIONS, KITS, AND USES FOR ANALYSIS OF NUCLEIC ACIDS COMPRISING REPEATING A/T-RICH SEGMENTS

The present application is a national stage application under 35 U.S.C. § 371 of International Application No. PCT/US2016/043503, filed Jul. 22, 2016, which designated the U.S. and claims the benefit of priority to U.S. Provisional Patent Application No. 62/196,239, filed Jul. 23, 2015, the entire contents of which are hereby incorporated by reference.

The present application contains a Sequence Listing which has been submitted electronically in ASCII format and is hereby incorporated by reference in its entirety. Said ASCII copy, created on Sep. 26, 2016, is named 10256_0050-00304_SL.txt and is 1,867 bytes in size.

This invention is in the field of nucleic acid analysis. In particular, the invention relates to improved methods for analyzing nucleic acids comprising repeating A/T-rich segments.

Many molecular biology techniques involve nucleic acid synthesis, e.g., synthesis of DNA or RNA. Nucleic acid synthesis therefore plays a central role in numerous biotechnological, medical, and research discovery applications. For example, polymerase chain reaction (PCR) is a DNA synthesis reaction that rapidly amplifies DNA template molecules. A typical PCR reaction mixture comprises primer sequences which are complementary to the ends of a desired template, deoxynucleotide triphosphates (dNTPs), various buffer components, and a DNA polymerase. The reaction mixture is admixed with a DNA sample known or suspected of harboring the desired template. The resulting mixture is then subjected through repeated cycles of template denaturation, primer annealing to the denatured template, and primer extension by the DNA polymerase, creating copies of the template. Because the product of each cycle can act as a template for subsequent reaction cycles, amplification generally proceeds in an exponential fashion. See, e.g., U.S. Pat. No. 4,683,202, and M. J. McPherson & S. G. Moller, PCR: The Basics (2nd Ed., Taylor & Francisco) (2006). PCR is a widely used technique due to its rapidity, low cost, sensitivity, and adaptability to high-throughput applications and automation.

A notable application of PCR is the detection and analysis of repetitive nucleotide sequences which can occur in the genome. Analysis of repeating A/T-rich segments, including homopolymeric repeat sequences of highly variable lengths (e.g., repeat length polymorphisms), can be useful for, e.g., genotyping, forensics, diagnostics, population genetics, and taxonomic studies.

For example, certain repeat length polymorphisms are known to be associated with disease states. Detection of such polymorphisms can therefore be helpful in disease diagnosis and treatment. For example, intron 6 of the TOMM40 gene contains a poly-T repeat length polymorphism (rs10524523), which has potential applications in Alzheimer's disease (AD) diagnosis. TOMM40 is also known as TOM40, PEREC-1, PER-EC1, C19orf1, D19S1177E, or P38.5. Three allelic categories were defined for this locus based on variation in its poly-T repeat length: Short (S, T≤19), Long (L, 20≤T≤29) and 'Very Long' (VL, T≥30). See Roses et. al., Alzheimer's & Dementia 9:132-136 (2013). The TOMM40 poly-T size polymorphism was recently reported as being associated with late-onset Alzheimer's disease (LOAD) and with cognitive performance in the elderly. See Roses et. al., The Pharmacogenetics Journal 10:375-384 (2010); Alzheimer's & Dementia 9:132-136 (2013).

An unfortunate limitation to the accuracy of DNA synthesis is the problem of polymerase slippage and stuttering. Repeating A/T-rich segments, such as homopolymeric nucleic acid segments (also referred to as mononucleotide repeat regions), are particularly susceptible to slippage and stuttering events. During polymerase slippage, the polymerase stalls and dissociates from the template strand during replication of the repeating A/T-rich segment, resulting in separation of the growing strand from the template strand. Slippage often then gives rise to polymerase stuttering, wherein the growing strand re-anneals to the template strand in an out-of-register manner such that one or more bases in either the growing or template strand are unpaired, forming a bubble. Such bubble formation at the growing or template strand results in expansion or truncation of the repeating A/T-rich segment, respectively (sometimes referred to as frameshift error). In particular, bubble formation on the growing or primer strand results in expansion of the repeating A/T-rich segment. And bubble formation on the template strand results in contraction of the repeating A/T-rich segment. Polymerase slippage and stuttering are known to cause high error rates in amplification and analysis of repeating A/T-rich segments. For example, slippage during PCR amplification can generate a complex mixture of amplicons of varying lengths, making it difficult to accurately determine the length of the repeating A/T-rich segment. As noted by Fazekas et. al. with respect to homopolymeric segments, "as the repeat number increases, the number of ambiguous bases increases disproportionately . . . to the point where sequence data cannot be used at all past the repeat." See Fazekas et. al., Taxon 59(3):694-697 at 694 (2010).

The difficulty due to slippage and stuttering may be compounded in the case of samples containing two alleles with repeating A/T-rich segments of similar lengths, e.g., lengths differing by a number of nucleotides such as 1, 2, 3, or 4. In such cases, slippage and stuttering may make it difficult to distinguish the products of the longer and shorter alleles, such that determining whether a sample is, e.g., homozygous for an allele with a repeating A/T-rich segment of length n or heterozygous for alleles with repeating A/T-rich segments of length n−1 and n+1 may not be possible, or may not be possible with high confidence.

Attempts have been made to mitigate the problem of slippage/stuttering. See Fazekas et al., BioTechniques 48:277-285 (2010). There, improved sequence quality was reported only for homopolymeric segments that are 15 nucleotides or less. "In . . . samples that possessed repeats greater than 15 bp, the sequence quality was not improved." See BioTechniques 48:277-285 at 695 (2010). Other attempts to improve amplification of homopolymeric segments by including a portion of the repeat region in the primer sequence were reported to "improve scoring of . . . repeats less than 20 bp." See Flores-Renteria et al., American Journal of Botany: e1-e3 (2011) at e2 (doi:10.3732/ajb.1000428).

Due to the issues of polymerase slippage/stuttering, TOMM40 poly-T polymorphisms are difficult to amplify and genotype, particularly those in the L (20≤T≤29) and VL (T≥30) categories. Because of this difficulty, researchers have been forced to engage in data manipulation in order to classify the polymorphic alleles. Such data manipulation includes, e.g., (1) calling only the most abundant peak in a complex distribution of amplicon sizes, or (2) using pattern recognition algorithms to match peak patterns to known genotypes (e.g., genotypes obtained from known clonal populations). Therefore, there exists a need for methods that reduce slippage/stutter, including methods that reduce slippage/stutter in synthesis of repeating A/T-rich segments such as homopolymeric segments, including long repeating A/T-rich segments or homopolymeric segments (e.g., greater than about 15 nucleotides, or about 20 nucleotides or greater). Such methods can be used for accurate analysis of nucleic acids containing repeating A/T-rich segments such as homopolymeric segments. Such methods can also be used for analysis of repeat length polymorphisms such as, e.g., the TOMM40 poly-T polymorphism.

In an embodiment, provided is a method of extending at least one nucleic acid template comprising a repeating A/T-rich segment, the method comprising performing a nucleic acid amplification reaction in an aqueous solution comprising the at least one nucleic acid template; at least one polymerase; at least one primer; magnesium; and NTPs in an AT/GC ratio of about 2 or higher; wherein the repeating A/T-rich segment is: (i) a homopolymeric segment comprising at least 10 A residues, at least 10 T residues, or at least 10 U residues, wherein the at least 10 A, T, or U residues are consecutive or interrupted once by one to three other nucleotides; or (ii) a segment comprising $(T_nA)_m$, $(AT_n)_m$, $(TA_n)_m$, or $(A_nT)_m$, wherein n is 2 or greater and m is such that the length of the repeating A/T-rich segment is 10 or more residues.

In an embodiment, provided is a method of amplifying at least one DNA template comprising a homopolymeric segment, the method comprising performing a DNA amplification reaction in an aqueous solution comprising the at least one DNA template; at least one hot-start DNA polymerase; at least two primers; magnesium at a concentration in the range from 1.5 mM to 3 mM; dNTPs in an AT/GC ratio of 5 or higher and a total concentration in the range from 1500 µM to 2500 µM; wherein the homopolymeric segment comprises at least 12 consecutive A residues or at least 12 consecutive T residues.

In an embodiment, provided is a method of detecting a genotype associated with late-onset Alzheimer's disease, comprising performing a DNA amplification reaction on at least one genetic locus associated with late-onset Alzheimer's disease, the genetic locus comprising a homopolymeric segment of at least 10 consecutive A residues or at least 10 consecutive T residues, wherein the DNA amplification reaction is performed in an aqueous solution comprising at least one DNA polymerase; at least two primers; magnesium; and dNTPs in an AT/GC ratio of 2 or higher; and wherein the DNA amplification reaction produces a product comprising a homopolymeric segment of at least 10 consecutive A residues or at least 10 consecutive T residues.

In an embodiment, provided is a kit comprising at least two distinct primers and NTPs in an AT/GC ratio greater than 2, the at least two primers being suitable for amplifying a genetic locus comprising either of (i) a homopolymeric segment of at least 10 consecutive A residues or at least 10 consecutive T residues or (ii) a repeating A/T-rich segment comprising $(T_nA)_m$, $(AT_n)_m$, $(TA_n)_m$, or $(A_nT)_m$, wherein n is 2 or greater and m is such that the length of the repeating A/T-rich segment is 10 or more residues.

In an embodiment, provided is a kit comprising reagents for use in amplifying at least one template comprising either of (i) a homopolymeric segment of at least 10 consecutive A residues or at least 10 consecutive T residues or (ii) a repeating A/T-rich segment comprising $(T_nA)_m$, $(AT_n)_m$, $(TA_n)_m$, or $(A_nT)_m$, wherein n is 2 or greater and m is such that the length of the repeating A/T-rich segment is 10 or more residues, wherein the reagents comprise NTPs in an AT/GC ratio greater than 2.

In an embodiment, provided is a reaction solution comprising at least one polymerase; one or more primers; magnesium; and NTPs in an AT/GC ratio of 2 or higher.

In an embodiment, provided is a use of NTPs in an AT/GC ratio of 2 or higher for amplifying a nucleic acid template comprising a repeating A/T-rich segment that is: (i) a homopolymeric segment of at least 10 A residues, at least 10 T residues, or at least 10 U residues, wherein the at least 10 A, T, or U residues are consecutive or interrupted once by one to three other nucleotides; or (ii) a segment comprising $(T_nA)_m$, $(AT_n)_m$, $(TA_n)_m$, or $(A_nT)_m$, wherein n is 2 or greater and m is such that the length of the repeating A/T-rich segment is 10 or more residues.

BRIEF DESCRIPTION OF DRAWING(S)

DETAILED DESCRIPTION

Figure 1A:
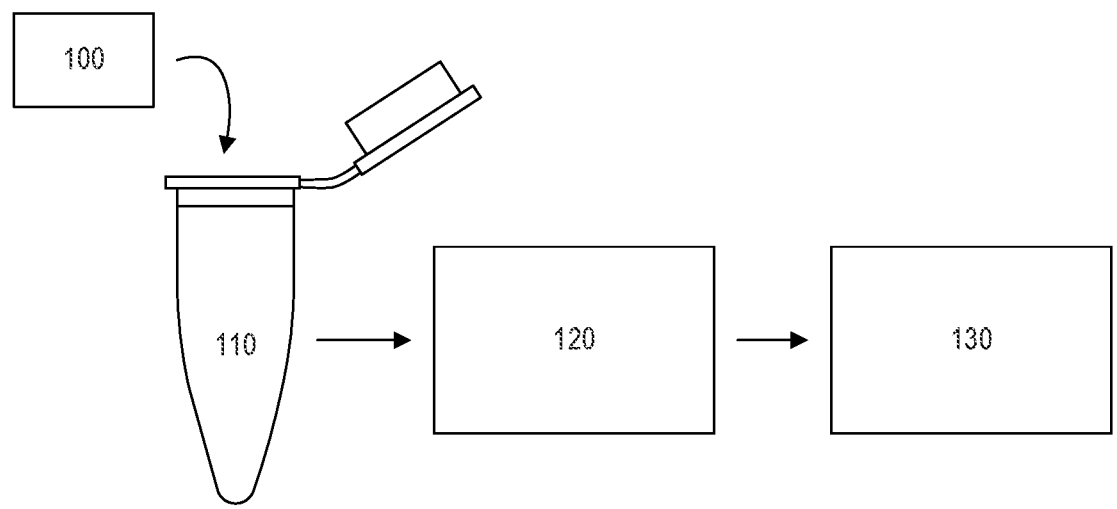
FIG. 1A depicts an exemplary workflow of a method disclosed herein.

The use of the word "a", "an" or "the" when used in conjunction with the term "comprising" in the claims and/or the specification can mean "one," but it is also consistent with the meaning of "one or more," "at least one," and "one or more than one." In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the endpoints.

The term "nucleotides" refers to molecules or ions capable of forming nucleic acids. Nucleotides can comprise a base moiety, a sugar moiety, and one or more phosphates (e.g., diphosphate or triphosphate). The sugar moiety can be deoxyribose, ribose, or another sugar moiety. The sugar moiety can be a modified sugar moiety, e.g., wherein one or more of the hydroxyl groups are replaced with halogen atoms or aliphatic groups, are functionalized as ethers, amines, or the like. Exemplary base moieties include purine and pyrimidine bases, and other heterocyclic bases that have been modified. Exemplary modified bases include, e.g., methylated purines, methylated pyrimidines, acylated purines or pyrimidines, alkylated riboses, and other heterocycles. Nucleotides can also comprise labeled moieties, such as those labeled with hapten, biotin, fluorescent, or chemiluminescent labels.

"NTP" refers to any nucleotide triphosphate, including ribonucleotide triphosphates (rNTPs) and deoxyribonucleotide triphosphates (dNTPs) and analogs of a nucleotide triphosphate. Deoxyribonucleotide triphosphates include, e.g., dATP, dCTP, dGTP, dTTP, dUTP, and analogs thereof. As used herein, a "dNTP mix" refers to a mix of two or more of dATP, dCTP, dCTP, dTTP, dUTP, and analogs thereof. Similarly, ribonucleotide triphosphates include, e.g., rATP, rCTP, rGTP, rTTP, rUTP, and analogs thereof. As used herein, an "rNTP mix" refers to a mix of two or more of rATP, rCTP, rCTP, rTTP, rUTP, and analogs thereof.

The term "AT/GC ratio" refers to the ratio of (i) the sum of the concentrations of ATP, TTP, UTP, and any analogs thereof, to (ii) the sum of the concentrations of CTP, GTP, and any analogs thereof, in a given solution or mixture. As noted above, an "NTP" includes rNTPs and dNTPs. Thus, for example, ATP includes rATP and dATP.

"Nucleotide analogs" refer to molecules or ions comprising a base moiety other than the natural bases adenine (A), cytosine (C), guanine (G), thymine (T), or uracil (U), a sugar moiety (which can be identical or similar to deoxyribose or ribose), and at least one phosphate or multiple phosphate (e.g., diphosphate or triphosphate) moiety. The nucleotide analog can be an analog of a specific nucleotide, such as ATP, CTP, GTP, TTP, or UTP, when it comprises a triphosphate and a sugar moiety, the structure and configuration of both of which are suitable for incorporation into a nucleic acid double helix by a polymerase, and a base whose base pairing properties in a nucleic acid double helix and loci of incorporation by DNA polymerases in a nucleic acid double helix are most similar to one of the five previously listed nucleotides, with the exception that analogs of TTP can also be analogs of UTP and vice versa.

The terms "template", "template strand", and "template nucleic acid" are used interchangeably herein to refer to a nucleic acid that is bound by a primer for extension by a nucleic acid synthesis reaction.

The term "locus" refers to a gene, nucleotide, or sequence on a chromosome. A locus can be "polymorphic" or exhibit a "polymorphism" if alternative forms of the locus exist in a population. An "allele" of a locus, as used herein, refers to a species of the locus.

The term "repeating A/T-rich segment" as used herein refers to a homopolymeric segment, defined below, or a segment comprising $(T_nA)_m$, $(AT_n)_m$, $(TA_n)_m$, or $(A_nT)_m$, wherein n is 2 or greater and m is such that the length of the repeating A/T-rich segment is 10 or more residues. The value of n need not be constant throughout the segment. Thus, examples of repeating A/T-rich segments include AATAATAATAAT (SEQ ID NO: 3), AATAAATAAT (SEQ ID NO: 4), AAATAAAAAT (SEQ ID NO: 5), AATAAAAAAT (SEQ ID NO: 6), etc. With respect to a segment comprising $(T_nA)_m$, $(AT_n)_m$, $(TA_n)_m$, or $(A_nT)_m$, in some embodiments, n is a value ranging from 2 to 10. In some embodiments, n is a value ranging from 3 to 10. In some embodiments, n is a value ranging from 4 to 10. In some embodiments, n is a value ranging from 2 to 8. In some embodiments, n is a value ranging from 3 to 8. In some embodiments, n is a value ranging from 4 to 8. In some embodiments, n is a value ranging from 2 to 6. In some embodiments, n is a value ranging from 3 to 6. In some embodiments, m is a value ranging from 2 to 20. In some embodiments, m is a value ranging from 3 to 20. In some embodiments, m is a value ranging from 4 to 20. In some embodiments, m is a value ranging from 2 to 15. In some embodiments, m is a value ranging from 3 to 15. In some embodiments, m is a value ranging from 4 to 15. In some embodiments, m is a value ranging from 2 to 10. In some embodiments, m is a value ranging from 3 to 10. In some embodiments, m is a value ranging from 4 to 10. In some embodiments, m is a value ranging from 2 to 8. In some embodiments, m is a value ranging from 3 to 8. In some embodiments, m is a value ranging from 4 to 8. In some embodiments, the length of the repeating A/T-rich segment is in the range from about 10 to about 60 residues. In some embodiments, the length of the repeating A/T-rich segment is in the range from about 10 to about 40 consecutive residues. In some embodiments, the length of the repeating A/T-rich segment is in the range from about 15 to about 40 consecutive residues. In some embodiments, the length of the repeating A/T-rich segment is in the range from about 20 to about 40 consecutive residues. In some embodiments, the length of the repeating A/T-rich segment is in the range from about 5 to about 50 consecutive residues. In some embodiments, the length of the repeating A/T-rich segment is in the range from about 10 to about 50 consecutive residues. In some embodiments, the length of the repeating A/T-rich segment is in the range from about 15 to about 50 consecutive residues. In some embodiments, the length of the repeating A/T-rich segment is in the range from about 20 to about 50 consecutive residues. In some embodiments, the length of the repeating A/T-rich segment is in the range from about 5 to about 60 consecutive residues. In some embodiments, the length of the repeating A/T-rich segment is in the range from about 10 to about 60 consecutive residues. In some embodiments, the length of the repeating A/T-rich segment is in the range from about 15 to about 60 consecutive residues. In some embodiments, the length of the repeating A/T-rich segment is in the range from about 20 to about 60 consecutive residues. Unless otherwise indicated, a repeating A/T-rich segment can comprise an interruption as explained in the following paragraph. In some embodiments, a repeating A/T-rich segment does not comprise an interruption.

The term "homopolymeric segment" as used herein refers to segments of nucleic acid which comprise a nucleotide such as A, T, or U repeated in series. Unless otherwise indicated, a homopolymeric segment can comprise an interruption in an otherwise consecutive series of nucleotides. The interruption can be 3 or fewer nucleotides differing from the other nucleotides making up the series. In some embodiments, the interruption is a single nucleotide. An example of a homopolymeric segment comprising an interruption is a first number of T residues, then one C residue, and then a second number of T residues. Another example of a homopolymeric segment comprising an interruption is a first number of U residues, then one C residue, and then a second number of U residues. Another example of a homopolymeric segment comprising an interruption is a first number of A residues, then one G residue, and then a second number of A residues. The first and second numbers of A, T, or U residues in the foregoing examples can be, e.g., in the range of 5 to 10. In some embodiments, the first and second numbers of A, T, or U residues in the foregoing examples are in the range of 6 to 10. In some embodiments, the first and second numbers of A, T, or U residues in the foregoing examples are in the range of 7 to 10. In some embodiments, the first and second numbers of A, T, or U residues in the foregoing examples are in the range of 8 to 10. In some embodiments, the first and second numbers of A, T, or U residues in the foregoing examples are in the range of 9 to 10. Alternatively, a homopolymeric segment can comprise a consecutive series of nucleotides (which is not interrupted).

The terms "variable length polymorphism", "size polymorphism", "repeat length polymorphism" can be used interchangeably to refer to polymorphisms in the length of a segment at a given locus.

FIG. 1A depicts an exemplary workflow of a method disclosed herein. The method can be used for the assessment of a nucleic acid comprising a homopolymeric segment. The method can comprise admixing a sample 100 with a reaction solution 110 to create a reaction mixture. The reaction solution 110 can be an aqueous solution. The sample 100 can be known or suspected to comprise a nucleic acid comprising a homopolymeric segment. The method can further comprise subjecting the reaction mixture to a reaction 120. The reaction 120 can comprise a nucleic acid synthesis reaction. The method can optionally further comprise performing an analysis 130 of a reaction product generated by the reaction 120.

Figure 1B:
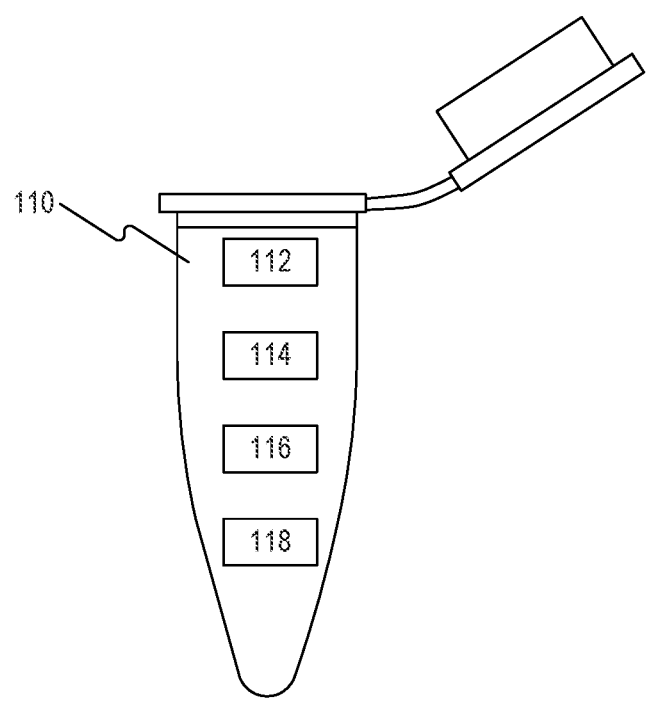
FIG. 1B depicts an exemplary reaction solution disclosed herein.

FIG. 1B depicts an exemplary reaction solution 110. The reaction solution 110 can comprise NTPs 112. In some embodiments, the NTPs comprise dNTPs. In some embodiments, the NTPs comprise rNTPs. The reaction solution 110 can further comprise a polymerase 114. The reaction solution can further comprise one or more primers 116. The reaction mixture can further comprise one or more additives 118.

The sample 100 can be a nucleic acid sample. The nucleic acid sample can be any substance containing or presumed to contain nucleic acid. The nucleic acid can be RNA, DNA, or any combination thereof. The DNA can be, e.g., genomic DNA, mitochondrial DNA, viral DNA, synthetic DNA, or cDNA reverse transcribed from RNA. The RNA can be rRNA, tRNA, mRNA, siRNA, shRNA, miRNA, snoRNA, primary transcript RNA, or synthetic RNA. A nucleic acid in the sample can be fused to one or more nucleic acid adaptors. In some embodiments, the adaptors are heterologous. An adaptor is heterologous if fusion of the adaptor to the nucleic acid results in a non-naturally occurring sequence. The adaptors can be, e.g., sequencing library adaptors or universal primer adaptors. The adaptors can comprise one or more barcodes. In some cases, a nucleic acid in the sample need not be ligated to one or more adaptors.

The nucleic acid sample can be a biological sample. The nucleic acid sample can be an enriched nucleic acid sample. The enriched nucleic acid sample can be derived from a biological sample that has undergone a purification process. In some embodiments, the nucleic acid is purified from a biological sample, e.g., by a process which comprises removing one or more non-nucleic acid components from the biological sample. The nucleic acid sample can comprise nucleic acid synthesized in vitro. Examples of in vitro nucleic acid synthesis include an amplification reaction such as PCR, in vitro transcription, in vitro reverse transcription, in vitro primer extension, a sequencing reaction, phosphoramidite-based nucleic acid synthesis, and combinations thereof.

The biological sample can comprise liquid. It can be a fluid sample. Exemplary fluid biological samples include, e.g., whole blood, plasma, serum, soluble cellular extract, extracellular fluid, cerebrospinal fluid, ascites, urine, sweat, tears, saliva, buccal sample, a cavity rinse, or an organ rinse. The biological sample can comprise a solid substance, e.g., feces or tissue. Exemplary tissues include, e.g., brain, bone, marrow, lung, heart, esophagus, stomach, duodenum, liver, prostate, nerve, meninges, kidneys, endometrium, cervix, breast, lymph node, muscle, hair, and skin, among others. The biological sample can be obtained from a living subject, or can be obtained from a subject post-mortem. The biological sample can comprise cell culture, cells, and/or cell components. For example, the biological sample can comprise cell culture constituents, such as, e.g., cultured cells, conditioned media, recombinant cells, and cell components. In some embodiments, the biological sample comprises cells. The cells can be primary cells, can be immortalized cells from a cell line, can be mammalian, or can be non-mammalian (e.g., bacteria, yeast). The biological sample can comprise a microbe, such as a virus, bacterium, protist, archaeon, or unicellular fungus. In some embodiments, the microbe is a virus. In some embodiments, the microbe is a bacterium. In some embodiments, the biological sample comprises cell components.

The biological sample can be obtained from a subject. The subject can be any biological entity comprising genetic material. The subject can be an animal, plant, fungus, or microorganism, such as, e.g., a bacterium, virus, archaeon, microscopic fungus, or protist. The subject can be a mammal. The mammal can be a human.

In some embodiments, the subject is not diagnosed with a disease. In some embodiments, the subject is diagnosed with a disease. In some embodiments, the subject is not suspected of being at risk for a disease. In some embodiments, the subject is suspected of being at risk for a disease. The disease can be a degenerative disorder. The degenerative disorder can be a neurodegenerative disorder. In some embodiments, the neurodegenerative disorder is Alzheimer's disease.

In some embodiments, the sample 100 is known to harbor or suspected of harboring a nucleic acid template. The nucleic acid template can comprise one or more repeating A/T-rich segments, such as homopolymeric segments. The nucleic acid template can be known to comprise one or more repeating A/T-rich segments, such as homopolymeric segments. The nucleic acid template can be suspected of comprising one or more repeating A/T-rich segments, such as homopolymeric segments.

The homopolymeric segment can comprise consecutive T and/or U residues (wherein the segment can contain consecutive T residues, consecutive U residues, or consecutive residues that include both U and T residues), called a "T-homopolymeric segment." The homopolymeric segment can comprise consecutive residues which are either (i) A or (ii) T and/or U residues, but not both (i) and (ii). The homopolymeric segment can comprise consecutive residues which are either (i) A or (ii) T residues, but not both (i) and (ii). The homopolymeric segment can comprise consecutive residues which are (i) A or (ii) U residues, but not both (i) and (ii). The homopolymeric segment can comprise consecutive A residues, called an "A-homopolymeric segment."

The homopolymeric segment can comprise consecutive T residues. The homopolymeric segment can comprise consecutive U residues.

The homopolymeric segment can comprise more than 10, more than 11, more than 12, more than 13, more than 14, more than 15, more than 16, more than 17, more than 18, more than 19, more than 20, more than 21, more than 22, more than 23, more than 24, more than 25, more than 26, more than 27, more than 28, more than 29, more than 30, more than 31, more than 32, more than 33, more than 34, more than 35, more than 36, more than 37, more than 38, more than 39, more than 40, more than 41, more than 42, more than 43, more than 44, more than 45, more than 46, more than 47, more than 48, more than 49, more than 50, more than 51, more than 52, more than 53, more than 54, more than 55, more than 56, more than 57, more than 58, more than 59, or more than 60 consecutive residues.

The homopolymeric segment can comprise a number of consecutive residues ranging from about 5 to about 40 consecutive residues. The homopolymeric segment can comprise a number of consecutive residues ranging from about 10 to about 40 consecutive residues. The homopolymeric segment can comprise a number of consecutive residues ranging from about 15 to about 40 consecutive residues. The homopolymeric segment can comprise a number of consecutive residues ranging from about 20 to about 40 consecutive residues. The homopolymeric segment can comprise a number of consecutive residues ranging from about 5 to about 50 consecutive residues. The homopolymeric segment can comprise a number of consecutive residues ranging from about 10 to about 50 consecutive residues. The homopolymeric segment can comprise a number of consecutive residues ranging from about 15 to about 50 consecutive residues. The homopolymeric segment can comprise a number of consecutive residues ranging from about 20 to about 50 consecutive residues. The homopolymeric segment can comprise a number of consecutive residues ranging from about 5 to about 60 consecutive residues. The homopolymeric segment can comprise a number of consecutive residues ranging from about 10 to about 60 consecutive residues. The homopolymeric segment can comprise a number of consecutive residues ranging from about 15 to about 60 consecutive residues. The homopolymeric segment can comprise a number of consecutive residues ranging from about 20 to about 60 consecutive residues. The homopolymeric segment can comprise a number of consecutive residues ranging from about 25 to about 40 consecutive residues. The homopolymeric segment can comprise a number of consecutive residues ranging from about 5 to about 38 consecutive residues. The homopolymeric segment can comprise a number of consecutive residues ranging from about 10 to about 38 consecutive residues. The homopolymeric segment can comprise a number of consecutive residues ranging from about 15 to about 38 consecutive residues. The homopolymeric segment can comprise a number of consecutive residues ranging from about 20 to about 38 consecutive residues. The homopolymeric segment can comprise a number of consecutive residues ranging from about 25 to about 38 consecutive residues. The homopolymeric segment can comprise a number of consecutive residues ranging from about 5 to about 36 consecutive residues. The homopolymeric segment can comprise a number of consecutive residues ranging from about 10 to about 36 consecutive residues. The homopolymeric segment can comprise a number of consecutive residues ranging from about 15 to about 36 consecutive residues. The homopolymeric segment can comprise a number of consecutive residues ranging from about 20 to about 36 consecutive residues. The homopolymeric segment can comprise a number of consecutive residues ranging from about 25 to about 36 consecutive residues.

The nucleic acid template can be known to comprise or suspected of comprising a locus. The locus can comprise a repeating A/T-rich segment, such as a homopolymeric segment. The locus can be known to comprise or suspected of comprising a polymorphism. The polymorphism can be a variable length polymorphism. The variable length polymorphism can be an A/T rich polymorphism. In some cases, the polymorphism is rs10524523. The locus can be in a gene. The gene can be associated with a disease. The disease can be a neurodegenerative disease. The neurodegenerative disease can be Alzheimer's disease. The Alzheimer's disease can be late-onset Alzheimer's disease. In some cases, the gene is TOMM40. In some cases, the locus is in intron 6 of TOMM40.

The NTPs 112 can comprise an AT/GC ratio. As used herein, an "AT/GC ratio" can refer to a ratio of the total concentration of the sum of nucleotide triphosphates comprising A, T, or U to the total concentration of the the sum of nucleotide triphosphates comprising G or C. For example, an "AT/GC" ratio can refer to a ratio of the total concentration of the sum of dATP, dUTP, and dTTP ([dATP]+[dUTP]+[dTTP]) to the total concentration of the sum of dGTP and dCTP (e.g., can equal ([dATP]+[dUTP]+[dTTP])/([dGTP]+[dCTP]). The AT/GC ratio can be biased, e.g., a ratio greater than 1. For example, the AT/GC ratio can be about 2, 2.5, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, or higher than 500.

The AT/GC ratio can be about 2 or higher, about 5 or higher, about 6 or higher, about 7 or higher, about 8 or higher, about 9 or higher, about 10 or higher, about 12.5 or higher, about 15 or higher, about 17.5 or higher, about 20 or higher, about 25 or higher, about 30 or higher, about 35 or higher, about 40 or higher, about 45 or higher, about 50 or higher, about 55 or higher, or about 60 or higher, about 70 or higher, about 80 or higher, about 90 or higher, about 100 or higher, about 120 or higher, about 140 or higher, about 160 or higher, about 180 or higher, about 200 or higher, about 250 or higher, about 300 or higher, about 350 or higher, about 400 or higher, about 450 or higher, or about 500 or higher.

The AT/GC ratio can range from about 2 to about 25, range from about 2 to about 60, range from about 5 to about 60, range from about 10 to about 40, range from about 15 to about 30, range from about 5 to about 25, range from about 8 to about 25, range from about 10 to about 25, range from about 15 to about 25, or range from about 18 to about 22. The AT/GC ratio can range from a value of about X to about Y, wherein X and Y have values described herein provided that Y is greater than X. X can be 2. X can be 5. X can be 10. X can be 15. X can be 18. X can be 20. X can be 22. X can be 25. X can be 30. X can be 35. X can be 40. X can be 45. X can be 50. X can be 55. X can be 60. X can be 70. X can be 80. X can be 90. X can be 100. X can be 120. X can be 140. X can be 160. X can be 180. X can be 200. X can be 250. X can be 300. X can be 350. X can be 400. X can be 450. Y can be 5. Y can be 10. Y can be 15. Y can be 18. Y can be 20. Y can be 22. Y can be 25. Y can be 30. Y can be 35. Y can be 40. Y can be 45. Y can be 50. Y can be 55. Y can be 60. Y can be 70. Y can be 80. Y can be 90. Y can be 100. Y can be 120. Y can be 140. Y can be 160. Y can be 180. Y can be 200. Y can be 250. Y can be 300. Y can be 350. Y can be 400. Y can be 450. Y can be 500.

The NTPs 112 can comprise one of, more than one of, or all of a dNTP complementary to cytidine, a dNTP complementary to guanosine, a dNTP complementary to adenosine, and a dNTP complementary to thymidine. For example, the NTPs 112 can comprise one of, more than one of, or all of dATP, dTTP, dCTP, dGTP, and dUTP. In some embodiments, the NTPs comprise dATP, dTTP, dCTP, and dGTP. In some embodiments, the NTPs comprise dATP. In some embodiments, the NTPs comprise a dNTP complementary to dATP. In some embodiments, the NTPs comprise dCTP. In some embodiments, the NTPs comprise a dNTP complementary to dCTP. In some embodiments, the NTPs comprise dGTP. In some embodiments, the NTPs comprise a dNTP complementary to dGTP. In some embodiments, the NTPs comprise dTTP. In some embodiments, the NTPs comprise a dNTP complementary to dTTP. In some embodiments, the NTPs comprise dUTP. In some embodiments, the NTPs comprise a dNTP complementary to dUTP. In some embodiments, the NTPs comprise diaminopurine. In some embodiments, the NTPs comprise 2-thiothymine. In some embodiments, the NTPs comprise 2-aminoadenine. In some embodiments, the NTPs comprise at least one dideoxy-NTP (ddNTP). In some embodiments, the NTPs comprise ddATP. In some embodiments, the NTPs comprise ddCTP. In some embodiments, the NTPs comprise ddGTP. In some embodiments, the NTPs comprise ddTTP. In some embodiments, the NTPs comprise ddUTP.

The NTP complementary to cytidine can be present at a concentration that is about 5 µM or greater. The NTP complementary to cytidine can be present at a concentration that is about 10 µM or greater. The NTP complementary to cytidine can be present at a concentration that is about 40 µM or greater. The NTP complementary to cytidine can be present at a concentration that ranges from about 10 µM to about 400 µM. The NTP complementary to cytidine can be present at a concentration that ranges from about 40 µM to about 400 µM. For example, the NTP complementary to cytidine can be present at a concentration that is about 10 µM, about 20 µM, about 30 µM, about 40 µM, about 41 µM, about 42 µM, about 43 µM, about 44 µM, about 45 µM, about 46 µM, about 47 µM, about 48 µM, about 49 µM, about 50 µM, about 51 µM, about 52 µM, about 53 µM, about 54 µM, about 55 µM, about 56 µM, about 57 µM, about 58 µM, about 59 µM, about 60 µM, about 61 µM, about 62 µM, about 63 µM, about 64 µM, about 65 µM, about 66 µM, about 67 µM, about 68 µM, about 69 µM, about 70 µM, about 71 µM, about 72 µM, about 73 µM, about 74 µM, about 75 µM, about 76 µM, about 77 µM, about 78 µM, about 79 µM, about 80 µM, about 81 µM, about 82 µM, about 83 µM, about 84 µM, about 85 µM, about 86 µM, about 87 µM, about 88 µM, about 89 µM, about 90 µM, about 91 µM, about 92 µM, about 93 µM, about 94 µM, about 95 µM, about 96 µM, about 97 µM, about 98 µM, about 99 µM, about 100 µM, about 125 µM, about 150 µM, about 175 µM, about 200 µM, about 225 µM, about 250 µM, about 275 µM, about 300 µM, about 325 µM, about 350 µM, about 375 µM, or about 400 µM.

The NTP complementary to guanosine can be present at a concentration that is about 5 µM or greater. The NTP complementary to guanosine can be present at a concentration that is about 10 µM or greater. The NTP complementary to guanosine can be present at a concentration that is about 40 µM or greater. The NTP complementary to guanosine can be present at a concentration that ranges from about 10 µM to about 400 µM. The NTP complementary to guanosine can be present at a concentration that ranges from about 40 µM to about 400 µM. For example, the NTP complementary to guanosine can be present at a concentration that is about 10 µM, about 20 µM, about 30 µM, about 40 µM, about 41 µM, about 42 µM, about 43 µM, about 44 µM, about 45 µM, about 46 µM, about 47 µM, about 48 µM, about 49 µM, about 50 µM, about 51 µM, about 52 µM, about 53 µM, about 54 µM, about 55 µM, about 56 µM, about 57 µM, about 58 µM, about 59 µM, about 60 µM, about 61 µM, about 62 µM, about 63 µM, about 64 µM, about 65 µM, about 66 µM, about 67 µM, about 68 µM, about 69 µM, about 70 µM, about 71 µM, about 72 µM, about 73 µM, about 74 µM, about 75 µM, about 76 µM, about 77 µM, about 78 µM, about 79 µM, about 80 µM, about 81 µM, about 82 µM, about 83 µM, about 84 µM, about 85 µM, about 86 µM, about 87 µM, about 88 µM, about 89 µM, about 90 µM, about 91 µM, about 92 µM, about 93 µM, about 94 µM, about 95 µM, about 96 µM, about 97 µM, about 98 µM, about 99 µM, about 100 µM, about 125 µM, about 150 µM, about 175 µM, about 200 µM, about 225 µM, about 250 µM, about 275 µM, about 300 µM, about 325 µM, about 350 µM, about 375 µM, or about 400 µM.

In some cases, a NTP complementary to cytidine and a NTP complementary to guanosine are both present at concentrations that are about 10 µM or greater. In some cases, a NTP complementary to cytidine and a NTP complementary to guanosine are both present at concentrations that are about 20 µM or greater. In some cases, a NTP complementary to cytidine and a NTP complementary to guanosine are both present at concentrations that are about 30 µM or greater. In some cases, a NTP complementary to cytidine and a NTP complementary to guanosine are both present at concentrations that are about 40 µM or greater. In some cases, the NTP complementary to cytidine and NTP complementary to guanosine are both present at concentrations that are between about 10 µM and 400 µM. In some cases, the NTP complementary to cytidine and NTP complementary to guanosine are both present at concentrations that are between about 40 µM and 400 µM.

The NTP complementary to adenosine can be present at a concentration that is about 20 µM or greater. For example, the NTP complementary to adenosine can be present at a concentration that is about 20 µM, about 30 µM, about 40 µM, about 50 µM, about 60 µM, about 70 µM, about 80 µM, about 90 µM, about 100 µM, about 125 µM, about 150 µM, about 175 µM, about 200 µM, about 225 µM, about 250 µM, about 275 µM, about 300 µM, about 325 µM, about 350 µM, about 375 µM, about 400 µM, about 425 µM, about 450 µM, about 475 µM, about 500 µM, about 525 µM, about 550 µM, about 575 µM, about 600 µM, about 625 µM, about 650 µM, about 675 µM, about 700 µM, about 725 µM, about 750 µM, about 775 µM, about 800 µM, about 825 µM, about 850 µM, about 875 µM, about 900 µM, about 925 µM, about 950 µM, about 975 µM, about 1000 µM (1 mM), about 1.2 mM, about 1.4 mM, about 1.6 mM, about 1.8 mM, about 2 mM, or higher. The NTP complementary to adenosine can be present at a concentration that ranges from about 20 µM and about 5 mM. The NTP complementary to adenosine can be present at a concentration that ranges from about 50 µM and about 5 mM. The NTP complementary to adenosine can be present at a concentration that ranges from about 100 µM and about 5 mM. The NTP complementary to adenosine can be present at a concentration that ranges from about 250 µM and about 5 mM. The NTP complementary to adenosine can be present at a concentration that ranges from about 20 µM and about 3 mM. The NTP complementary to adenosine can be present at a concentration that ranges from about 50 µM and about 3 mM. The NTP complementary to adenosine can be present at a concentration that ranges from about 100 µM and about 3 mM. The NTP complementary to adenosine can be present at a concentration that ranges from about 250 µM and about 3 mM. The NTP complementary to adenosine can be present at a concentration that ranges from about 20 µM and about 2 mM. The NTP complementary to adenosine can be present at a concentration that ranges from about 50 µM and about 2 mM. The NTP complementary to adenosine can be present at a concentration that ranges from about 100 µM and about 2 mM. The NTP complementary to adenosine can be present at a concentration that ranges from about 250 µM and about 2 mM. The NTP complementary to adenosine can be present at a concentration that ranges from about 700 µM and about 1.5 mM. The NTP complementary to adenosine can be present at a concentration that ranges from about 700 µM and about 2 mM.

The NTP complementary to thymidine can be present at a concentration that is about 20 µM or greater. For example, the NTP complementary to thymidine can be present at a concentration that is about 20 µM, about 30 µM, about 40 µM, about 50 µM, about 60 µM, about 70 µM, about 80 µM, about 90 µM, about 100 µM, about 125 µM, about 150 µM, about 175 µM, about 200 µM, about 225 µM, about 250 µM, about 275 µM, about 300 µM, about 325 µM, about 350 µM, about 375 µM, about 400 µM, about 425 µM, about 450 µM, about 475 µM, about 500 µM, about 525 µM, about 550 µM, about 575 µM, about 600 µM, about 625 µM, about 650 µM, about 675 µM, about 700 µM, about 725 µM, about 750 µM, about 775 µM, about 800 µM, about 825 µM, about 850 µM, about 875 µM, about 900 µM, about 925 µM, about 950 µM, about 975 µM, about 1000 µM (1 mM), about 1.2 mM, about 1.4 mM, about 1.6 mM, about 1.8 mM, about 2 mM, or higher. The NTP complementary to thymidine can be present at a concentration that ranges from about 20 µM and about 5 mM. The NTP complementary to thymidine can be present at a concentration that ranges from about 50 µM and about 5 mM. The NTP complementary to thymidine can be present at a concentration that ranges from about 100 µM and about 5 mM. The NTP complementary to thymidine can be present at a concentration that ranges from about 250 µM and about 5 mM. The NTP complementary to thymidine can be present at a concentration that ranges from about 20 µM and about 3 mM. The NTP complementary to thymidine can be present at a concentration that ranges from about 50 µM and about 3 mM. The NTP complementary to thymidine can be present at a concentration that ranges from about 100 µM and about 3 mM. The NTP complementary to thymidine can be present at a concentration that ranges from about 250 µM and about 3 mM. The NTP complementary to thymidine can be present at a concentration that ranges from about 20 µM and about 2 mM. The NTP complementary to thymidine can be present at a concentration that ranges from about 50 µM and about 2 mM. The NTP complementary to thymidine can be present at a concentration that ranges from about 100 µM and about 2 mM. The NTP complementary to thymidine can be present at a concentration that ranges from about 250 µM and about 2 mM. The NTP complementary to thymidine can be present at a concentration that ranges from about 700 µM and about 1.5 mM. The NTP complementary to thymidine can be present at a concentration that ranges from about 700 µM and about 2 mM.

In some cases, a NTP complementary to adenosine and a NTP complementary to thymidine are both present at concentrations that are about 20 µM or greater, about 50 µM or greater, about 150 µM or greater, about 200 µM or greater, about 250 µM or greater, about 500 µM or greater, about 750 µM or greater, about 1000 µM or greater, about 2000 µM or greater, about 3000 µM or greater or about 4000 µM or greater. In some cases, the NTP complementary to adenosine and NTP complementary to thymidine are both present at concentrations that are between about 50 µM and about 4000 µM. In some cases, the NTP complementary to adenosine and NTP complementary to thymidine are both present at concentrations that are between about 250 µM and about 2000 µM. In some cases, the NTP complementary to adenosine and NTP complementary to thymidine are both present at concentrations that are between about 700 µM and 1500 µM. In some cases, the NTP complementary to adenosine and NTP complementary to thymidine are both present at concentrations that are between about 700 µM and 2000 µM.

The reaction solution 110 can comprise a total NTP concentration. The total NTP concentration can be about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 1.2 mM, about 1.5 mM, about 2 mM, about 2.1 mM, about 2.2. mM, about 2.3 mM, about 2.4 mM, about 2.5 mM, about 2.6 mM, about 2.7 mM, about 2.8 mM, about 2.9 mM, about 3 mM, about 3.1 mM, about 3.2 mM, about 3.3 mM, about 3.4 mM, about 3.5 mM, about 3.6 mM, about 3.7 mM, about 3.8 mM, about 3.9 mM, about 4 mM, about 4.1 mM, about 4.2 mM, about 4.3 mM, about 4.4 mM, about 4.5 mM, about 4.6 mM, about 4.7 mM, about 4.8 mM, about 4.9 mM, about 5 mM, about 5.1 mM, about 5.2 mM, about 5.3 mM, about 5.4 mM, about 5.5 mM, about 5.6 mM, about 5.7 mM, about 5.8 mM, about 5.9 mM, about 6 mM, about 6.1 mM, about 6.2 mM, about 6.3 mM, about 6.4 mM, about 6.5 mM, about 6.6 mM, about 6.7 mM, about 6.8 mM, about 6.9 mM, about 7 mM, about 7.1 mM, about 7.2 mM, about 7.3 mM, about 7.4 mM, about 7.5 mM, about 7.6 mM, about 7.7 mM, about 7.8 mM, about 7.9 mM, about 8 mM, about 8.1 mM, about 8.2 mM, about 8.3 mM, about 8.4 mM, about 8.5 mM, about 8.6 mM, about 8.7 mM, about 8.8 mM, about 8.9 mM, about 9 mM, about 9.1 mM, about 9.2 mM, about 9.3 mM, about 9.4 mM, about 9.5 mM, about 9.6 mM, about 9.7 mM, about 9.8 mM, about 9.9 mM, about 10 mM, about 10.1 mM, about 10.2 mM, about 10.3 mM, about 10.4 mM, about 10.5 mM, about 10.6 mM, about 10.7 mM, about 10.8 mM, about 10.9 mM, or about 11 mM. In some cases, the total NTP concentration is about 2.1 mM. In some cases, the total NTP concentration is about 4.1 mM. In some cases, the total NTP concentration is about 6.1 mM. In some cases, the total NTP concentration is about 4.2 mM.

In some cases, the total NTP concentration ranges from about 0.4 mM to about 8 mM. In some cases, the total NTP concentration ranges from about 0.5 mM to about 5 mM. In some cases, the total NTP concentration ranges from about 2 mM to about 4.5 mM. In some cases, the total NTP concentration ranges from about 2 mM to about 2.5 mM. In some cases, the total NTP concentration ranges from about 2.5 mM to about 3.5 mM. In some cases, the total NTP concentration ranges from about 3.5 mM to about 4.5 mM. In some cases, the total NTP concentration ranges from about 3.5 mM to about 4.2 mM.

The polymerase 114 can be a DNA polymerase. The DNA polymerase can comprise a wild-type polymerase. The DNA polymerase can comprise a modified polymerase. The DNA polymerase can comprise a thermophilic polymerase. The DNA polymerase can comprise a chimeric polymerase. The DNA polymerase can comprise an engineered polymerase. The DNA polymerase can comprise a mixture of more than one polymerase. Exemplary DNA polymerases include, e.g., a high-fidelity DNA polymerase (EXACT POLYMERASE™ (5 PRIME GmbH), ACCUSURE™ DNA Polymerase (Bioline), PHUSION™ ACCUPRIME™ Pfx (Invitrogen), Extensor Hi-Fidelity PCR Enzyme (ABgene), ACCUZYME™ DNA Polymerase (Bioline), OPTIMASE® DNA Polymerase (Transgenomic, Inc.), VELOCITY DNA Polymerase (Bioline), GENECHOICE® ACCUPOL™ DNA Polymerase (GeneChoice, Inc.), KOD HIFI™ DNA Polymerase (Novagen), EASY-A™ High-Fidelity PCR Cloning Enzyme (Stratagene), EXL™ DNA Polymerase (Stratagene), KAPA HIFI™ DNA Polymerase (Kapa Biosystems), HERCULASE® II Fusion DNA Polymerase (Stratagene), BIO-X-ACT™ Long DNA Polymerase (Bioline), BIO-X-ACT™ Short DNA Polymerase (Bioline), EU-Taq DNA Polymerase (EENZYME® LLC), PYROPHAGE® 3173 DNA Polymerase, Pwo DNA Polymerase (Roche Applied Science), or PLATINUM® Taq DNA Polymerase High Fidelity (Invitrogen)), a hot-start DNA polymerase (PHIRE™ Hot Start DNA Polymerase (New England Biolabs), PHUSION™ Hot Start High-Fidelity DNA Polymerase (New England Biolabs), JUMPSTART™ REDTAQ™ DNA Polymerase (Sigma-Aldrich), PFUULTRA™ Hotstart DNA Polymerase (Stratagene), PFUTURBO® Cx Hotstart DNA Polymerase (Stratagene), PRIMESTAR™ HS DNA Polymerase (Takara), HotMaster™ Taq DNA Polymerase (5 PRIME GmbH), HOTTAQ™ DNA Polymerase (Abnova Corporation), AMPLITAQ GOLD® DNA Polymerase (Applied Biosystems), RED HOT® DNA Polymerase (ABgene), ACCUPRIME™ GC-Rich DNA Polymerase (Invitrogen), PAQ5000™ DNA Polymerase (Stratagene), or SAHARA™ DNA Polymerase (Bioline)), a mixture of more than one polymerase (GENECHOICE® UNIPOL™ DNA Polymerase (GeneChoice, Inc.), KOD XL™ DNA Polymerase (Novagen), LA TAQ DNA Polymerase (Takara), EXPAND® 20 kb PLUS Thermostable DNA polymerase mixture (Roche Applied Science), EXPAND® High Fidelity PLUS Thermostable DNA polymerase mixture (Roche Applied Science), EXPAND® High Fidelity Thermostable DNA polymerase mixture (Roche Applied Science), EXPAND® Long Template Thermostable DNA polymerase mixture (Roche Applied Science), HERCULASE® Enhanced DNA Polymerase (Stratagene), KAPA LONGRANGE™ DNA Polymerase (Kapa Biosystems), Synergy Taq DNA Polymerase (EENZYME® LLC), or ELONGASE® Enzyme Mix (Invitrogen)), a chimeric DNA polymerase (PFX50™ DNA Polymerase (Invitrogen), BIOLINE HYBRIPOL™ DNA Polymerase (Bioline), or PHUSION™ DNA Polymerase (New England Biolabs)), a modified DNA polymerase (KAPA2G™ Robust DNA Polymerase (Kapa Biosystems), KAPA2G™ Robust HotStart DNA Polymerase (Kapa Biosystems), KAPA2G™ Fast DNA Polymerase (Kapa Biosystems), KAPA2G™ Fast Hot-Start DNA Polymerase (Kapa Biosystems), 9 DEGREES NORTH™ (Modified) DNA Polymerase (New England Biolabs), or THERMINATOR™ DNA Polymerase (New England Biolabs)), an exo-DNA polymerase (Exo-Pfu DNA Polymerase (Stratagene), Bst DNA Polymerase Lg Frag (New England Biolabs), MASTERAMP™ Tfl DNA Polymerase (EPICENTRE Biotechnologies), Thermoprime Plus DNA Polymerase (ABgene), Taq-red DNA Polymerase (AppliChem GmbH), BIOTHERM™ Taq DNA Polymerase (EENZYME® LLC), GENECHOICE® REDPOL™ DNA Polymerase (GeneChoice, Inc.), or Exo Minus (Lucigen)), a high-yield DNA polymerase (YIELDACE™ DNA Polymerase (Stratagene) or E2TAK™ DNA Polymerase (Takara)), or naturally occurring DNA polymerases from *P. kodakaraensis, P. furiosus, T. gorgonarius, T. zilligii, T. litoralis* "Vent™", P. GB-D "Deep Vent", T. 9N-7, *T. aggregans, T. barossii, T. fumicolans, T. celer, Pyrococcus* sp. strain ST700, *T. pacificus, P. abysii, T. profundus, T. siculi, T. hydrothermalis, Thermococcus* sp. strain GE8, *T. thioreducens, P. horikoshii* or *T. onnurineus* NA1, *Thermococcus* sp. 9° N-7, *Thermococcus* sp. GI-J, *Thermococcus* sp. MAR-13, *Thermococcus* sp. GB-C, *Thermococcus* sp. GI-H, *Thermus aquaticus, Thermus thermophilus, Thermus caldophilus, Thermus filiformis, Thermus flavus, Thermotoga maritima, Bacillus stearothermophilus*, or *Bacillus caldotenax*, for example. In certain embodiments, the DNA polymerase is Phoenix Hot Start Taq Polymerase®. In certain embodiments, the DNA polymerase is Phusion$^a$ Hot Start High-Fidelity DNA Polymerase (New England Biolabs). In certain embodiments, the DNA polymerase is Herculase® II Fusion DNA Polymerase (Stratagene).

The DNA polymerase can be a hot-start DNA polymerase. Exemplary hot-start DNA polymerases include, e.g., Phoenix Hot Start Taq Polymerase® (Enzymatics), Phire™ Hot Start DNA Polymerase (New England Biolabs), Phusion$^a$ Hot Start High-Fidelity DNA Polymerase (New England Biolabs), JumpStart™ REDTaq™ DNA Polymerase (Sigma-Aldrich), PfuUltra™ Hotstart DNA Polymerase (Stratagene), PfuTurbo® Cx Hotstart DNA Polymerase (Stratagene), PrimeSTAR™ HS DNA Polymerase (Takara), among others. In some cases, the polymerase 114 is an RNA polymerase.

One or more primers 116 can prime polymerase-mediated extension into, across, or within a locus. The one or more primers 116 can hybridize to a template comprising the locus. The one or more primers 116 can amplify the template comprising the locus. Exemplary loci are described herein. The locus can be known to harbor or suspected of harboring a segment that comprises one or more homopolymeric segments. Exemplary homopolymeric segments are described herein.

The one or more primers 116 can comprise a forward primer. The forward primer can anneal to a 5' end of a template. For example, the forward primer can anneal to about 15-30, 15-25, 15-20, 20-30, or 20-25 nucleotides at a 5' end of the template. The one or more primers can also comprise a reverse primer. The reverse primer can anneal to a 3' end of a template (e.g., to a 5' end of a reverse strand of the template). For example, the reverse primer can anneal to about 15-30, 15-25, 15-20, 20-30, or 20-25 nucleotides at a 3' end of the template.

The one or more primers 116 can comprise a first primer that hybridizes to a location upstream of a variable length polymorphism. In some cases, a portion of the first primer can hybridize to a portion of the variable length polymorphism. The one or more primers 116 can comprise a second primer that hybridizes to a location downstream of the variable length polymorphism. In some cases, a portion of the second primer can hybridize to a portion of the variable length polymorphism. The second primer can hybridize to a portion of the variable length polymorphism that is smaller than the smallest known allele of the variable length polymorphism. For instance, if the smallest known allele of a variable length polymorphism of interest is 10 nucleotides, the second primer can hybridize to 9 or fewer nucleotides of the variable length polymorphism. In some cases, a first or second primer can comprise a 3'-terminal sequence that preferentially hybridizes to about 4 to about 9 consecutive A or T residues.

The variable length polymorphism can be a TOMM40 polymorphism. In some embodiments, the variable length polymorphism is the rs10524523 polymorphism.

In some embodiments, the one or more primers 116 comprises a first primer that hybridizes to a location upstream of a variable length polymorphism, such as within 500, 300, 200, 100, or 50 nucleotides of the variable length polymorphism. In some embodiments, the first primer specifically hybridizes to a location separated from a variable length polymorphism by 1 to about 500 nucleotides. In some embodiments, the first primer specifically hybridizes to a location separated from a variable length polymorphism by 1 to about 300 nucleotides. In some embodiments, the first primer specifically hybridizes to a location separated from a variable length polymorphism by 1 to about 200 nucleotides. In some embodiments, the first primer specifically hybridizes to a location separated from a variable length polymorphism by 1 to about 100 nucleotides. In some embodiments, the first primer specifically hybridizes to a location separated from a variable length polymorphism by 1 to about 50 nucleotides. In some embodiments, the first primer specifically hybridizes to a location separated from a variable length polymorphism by about 50 to about 500 nucleotides. In some embodiments, the first primer specifically hybridizes to a location separated from a variable length polymorphism by about 50 to about 300 nucleotides. In some embodiments, the first primer specifically hybridizes to a location separated from a variable length polymorphism by about 50 to about 200 nucleotides. In some embodiments, the first primer specifically hybridizes to a location separated from a variable length polymorphism by about 50 to about 100 nucleotides. The one or more primers 116 can comprise a second primer that hybridizes to a location downstream of the variable length polymorphism, such as within 500, 300, 200, 100, or 50 nucleotides of the variable length polymorphism. In some embodiments, the second primer specifically hybridizes to a location separated from a variable length polymorphism by 1 to about 500 nucleotides. In some embodiments, the second primer specifically hybridizes to a location separated from a variable length polymorphism by 1 to about 300 nucleotides. In some embodiments, the second primer specifically hybridizes to a location separated from a variable length polymorphism by 1 to about 200 nucleotides. In some embodiments, the second primer specifically hybridizes to a location separated from a variable length polymorphism by 1 to about 100 nucleotides. In some embodiments, the second primer specifically hybridizes to a location separated from a variable length polymorphism by 1 to about 50 nucleotides. In some embodiments, the second primer specifically hybridizes to a location separated from a variable length polymorphism by about 50 to about 500 nucleotides. In some embodiments, the second primer specifically hybridizes to a location separated from a variable length polymorphism by about 50 to about 300 nucleotides. In some embodiments, the second primer specifically hybridizes to a location separated from a variable length polymorphism by about 50 to about 200 nucleotides. In some embodiments, the second primer specifically hybridizes to a location separated from a variable length polymorphism by about 50 to about 100 nucleotides. The variable length polymorphism can be a TOMM40 polymorphism. In some embodiments, the variable length polymorphism is the rs10524523 polymorphism. Specific hybridization to a location means that a primer preferentially binds to that location over other locations in the sample under a primer binding condition suitable for a nucleic acid synthesis reaction, such as a solution comprising 50 mM KCl, pH 8, at one or more hybridization temperatures such as 42° C., 45° C., 50° C., 55° C., 56° C., 57° C., 58° C., 59° C., 60° C., 61° C., 62° C., 63° C., 64° C., 65° C., 66° C., 67° C., 68° C., 69° C., 70° C., 71° C., or 72° C.

Exemplary primers include, e.g., CCAAAGCATTGG-GATTACTGGC (primer 001) (SEQ ID NO: 1) and GAT-TGCTTGAGCCTAGGCATTC (primer 002) (SEQ ID NO: 2). In some embodiments, primer 001 is detectably labeled. In some embodiments, primer 001 is detectably labeled with a fluorophore. In some embodiments, primer 001 is detectably labeled with FAM. In some embodiments, primer 002 is detectably labeled. In some embodiments, primer 002 is detectably labeled with a fluorophore. In some embodiments, primer 002 is detectably labeled with FAM.

In some embodiments, the one or more primers 116 comprises a set of primers. The set of primers can comprise at least one primer described herein. In some embodiments, the set of primers is capable of priming polymerase-mediated extension into more than one locus. In some embodiments, the set of primers comprises primers collectively capable of hybridizing specifically to a plurality of templates that comprise or are suspected of harboring a locus of interest. In some embodiments, the set of primers is capable of amplifying a plurality of templates comprising a plurality of loci of interest.

The one or more additives 118 can comprise a buffer. Exemplary buffers include, e.g., tris(hydroxymethyl)aminomethane (Tris), bis-tris propane, bicarbonate, phosphate, glycine, histidine, 4-(2-hydroxyethyl)-1-piperazineethanesulfonic acid (HEPES), 3-(N-morpholino)propanesulfonic acid (MOPS), and various conjugate bases/acids and salts thereof.

The one or more additives 118 can comprise magnesium (Mg). The term magnesium, as used herein, includes magnesium in solution (solute and solvated/hydrated forms) and in its ionized forms. The magnesium can be in the form of a magnesium salt, including solute and solvated/hydrated forms, e.g., magnesium ions and counterions in solution. The magnesium salt can be a chemical compound containing magnesium and the conjugate base of an acid. Exemplary magnesium salts include, without limitation, magnesium chloride, magnesium acetate, magnesium sulfate, magnesium bromide, or magnesium iodide. The magnesium salts can be provided in such quantity that the final concentration of magnesium can be in a given range. In some embodiments, the magnesium concentration ranges from about 1 to about 11 mM. In some embodiments, the magnesium concentration ranges from about 1 to about 10 mM. In some embodiments, the magnesium concentration ranges from about 1 to about 7.5 mM. In some embodiments, the magnesium concentration ranges from about 1 to about 5 mM. In some embodiments, the magnesium concentration ranges from about 1 to about 4.5 mM. In some embodiments, the magnesium concentration ranges from about 1 to about 4 mM. In some embodiments, the magnesium concentration ranges from about 1 to about 3.5 mM. In some embodiments, the magnesium concentration ranges from about 1 to about 3 mM. In some embodiments, the magnesium concentration ranges from about 1.5 to about 3 mM. In some embodiments, the magnesium concentration ranges from about 2 to about 5 mM. In some embodiments, the magnesium concentration ranges from about 2 to about 11 mM. In some embodiments, the magnesium concentration ranges from about 2 to about 10 mM. In some embodiments, the magnesium concentration ranges from about 2 to about 7.5 mM. In some embodiments, the magnesium concentration ranges from about 2.5 to about 11 mM. In some embodiments, the magnesium concentration ranges from about 2.5 to about 10 mM. In some embodiments, the magnesium concentration ranges from about 2.5 to about 7.5 mM. In some embodiments, the magnesium concentration ranges from about 2.5 to about 5 mM. In some embodiments, the magnesium concentration ranges from about 3 to about 11 mM. In some embodiments, the magnesium concentration ranges from about 3 to about 10 mM. In some embodiments, the magnesium concentration ranges from about 3 to about 7.5 mM. In some embodiments, the magnesium concentration ranges from about 3 to about 5 mM. In some embodiments, the magnesium concentration ranges from about 1.5 to about 4.5 mM. In some embodiments, the magnesium concentration ranges from about 2 to about 4 mM. For example, the final concentration of magnesium can be about 1, 1.5, 2, 2.5, 3, 3.5, 4, 4.5, 5, 6, 7, 8, 9, 10, or 11 mM. In some embodiments, the magnesium concentration ranges from about 1 mM to 7 mM more than the total NTP concentration. In some embodiments, the magnesium concentration ranges from about 1 mM to 6 mM more than the total NTP concentration. In some embodiments, the magnesium concentration ranges from about 1 mM to 5 mM more than the total NTP concentration. In some embodiments, the magnesium concentration ranges from about 1 mM to 4 mM more than the total NTP concentration. In some embodiments, the magnesium concentration ranges from about 1 mM to 3 mM more than the total NTP concentration. In some embodiments, the magnesium concentration ranges from about 1 mM to 2 mM more than the total NTP concentration. In some embodiments, the magnesium concentration ranges from about 1 mM to 1 mM more than the total NTP concentration. The magnesium can be present at a molarity that ranges from about 70% to about 300% of the molarity of total NTPs. The magnesium can be present at a molarity that ranges from about 80% to about 300% of the molarity of total NTPs. The magnesium can be present at a molarity that ranges from about 70% to about 250% of the molarity of total NTPs. The magnesium can be present at a molarity that ranges from about 80% to about 250% of the molarity of total NTPs. The magnesium can be present at a molarity that ranges from about 70% to about 200% of the molarity of total NTPs. The magnesium can be present at a molarity that ranges from about 80% to about 200% of the molarity of total NTPs. The magnesium can be present at a molarity that ranges from about 70% to about 150% of the molarity of total NTPs. The magnesium can be present at a molarity that ranges from about 80% to about 150% of the molarity of total NTPs. The magnesium can be present at a molarity that ranges from about 90% to about 125% of the molarity of total NTPs.

The one or more additives 118 can comprise one or more enhancers. In some cases, the one or more enhancers comprises one or more of betaine, DMSO, and a neutral detergent. In some cases, the one or more enhancers comprises one or more of betaine, a betaine analog, DMSO, and a neutral detergent. "Betaine" refers to N,N,N-trimethylglycine. A "betaine analog" is any neutral chemical compound with a positively charged cationic functional group which bears no hydrogen atom, for example, an ammonium ion or phosphonium ion, and with a negatively charged functional group such as a carboxylate group which may not be adjacent to the cationic site. In some embodiments, the betaine analog has a molecular weight less than or equal to about 600 Da. The betaine analog can have a molecular weight less than or equal to about 300 Da. The betaine analog can have a molecular weight ranging from about 75 to about 600 Da. The betaine analog can have a molecular weight ranging from about 75 to about 300 Da. Additionally or alternatively, the betaine analog can comprise an ammonium moiety and/or a carboxylate moiety. The one or more additives 118 can comprise betaine and/or a betaine analog. Betaine and/or a betaine analog can be present at a molar concentration ranging from 0.01 to 5 M, 0.01 to 4 M, 0.01 to 3 M, 0.01 to 2.5 M, 0.02 to 5 M, 0.03 to 5 M, 0.04 to 5 M, 0.05 to 5 M, 0.07 to 5 M, 0.1 to 5 M, 0.2 to 5 M, 0.3 to 5 M, 0.4 to 5 M, 0.5 to 5 M, 0.7 to 5 M, 1 to 5 M, 1.5 to 5 M, 0.1 to 4 M, 0.5 to 3 M, 0.5 to 2.5 M, or 0.5 to 2.5 M, for example, about 0.01, 0.02, 0.05, 0.1, 0.2, 0.5, 0.75, 1, 1.25, 1.5, 1.6, 1.7, 1.8, 1.9, 2.0, 2.1, 2.2, 2.3, 2.4, 2.5, 3, 3.5, 4, 4.5, or 5 M. In some cases, the one or more additives 118 comprise about 1 M betaine.

The one or more additives 118 can comprise DMSO. DMSO can be present in the reaction solution at a concentration that ranges from about 0.1% to about 10% (v/v). DMSO can be present in the reaction solution at a concentration that ranges from about 0.5% to about 5%. DMSO can be present in the reaction solution at a concentration that ranges from about 0.5% to about 10%. DMSO can be present in the reaction solution at a concentration that ranges from about 0.1% to about 5%. DMSO can be present in the reaction solution at a concentration that ranges from about 0.5% to about 3%. The DMSO can be present in the reaction solution at a concentration that is about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, or about 10%. In some cases, the one or more additives 118 comprise about 1% DMSO. In some cases, the one or more additives 118 comprise about 2% DMSO.

In some cases, the reaction solution comprises two enhancers. In some cases, the reaction solution comprises three enhancers. In some cases, the reaction solution comprises betaine and DMSO. In some cases, the reaction solution comprises a betaine analog and DMSO. In some cases, the reaction solution comprises betaine, DMSO, and a neutral detergent. Exemplary concentrations of betaine and DMSO are disclosed herein.

Other additives that can be present in the reaction solution include, but are not limited to, non-specific background/blocking nucleic acids (e.g., salmon sperm DNA), biopreservatives (e.g. sodium azide), and inhibitors (e.g. RNAse inhibitors).

Some embodiments of a reaction solution 110 comprise a NTPs 112 with an AT/GC ratio of about 2 or greater. In some embodiments, the reaction solution comprises about 100 µM each dATP and dTTP, and 50 µM each dGTP and dCTP. In some embodiments, the NTPs 112 have an AT/GC ratio of about 5. In some embodiments, the reaction solution comprises about 250 µM each dATP and dTTP, and 50 µM each dGTP and dCTP. In some embodiments, the NTPs 112 have an AT/GC ratio of about 10. In some embodiments, the reaction solution comprises about 500 µM each dATP and dTTP, and 50 µM each dGTP and dCTP. In some embodiments, the NTPs 112 have an AT/GC ratio of about 20. For example, the reaction solution can comprise about 1000 µM each dATP and dTTP, and 50 µM each dGTP and dCTP. In some embodiments, the reaction solution comprises about 2000 µM each dATP and dTTP, and 100 µM each dGTP and dCTP.

The reaction solution can further comprise about 1.5 mM to about 4 mM $Mg^{2+}$. In some embodiments, the reaction solution comprises about 2.5 mM $Mg^{2+}$. In some embodiments, the reaction solution comprises about 2 mM $Mg^{2+}$. In some embodiments, the reaction solution comprises about 4 mM $Mg^{2+}$. The reaction solution can further comprise betaine. The betaine can be present in a molarity that ranges from about 0.1 to 2 M betaine, for example, between about 0.5 to about 1.5 M betaine. In some embodiments, the betaine is present at a 1 M concentration. The reaction solution can further comprise DMSO. The DMSO can be present at a concentration that can be between about 0.1% and about 10%, for example, between about 0.5% and about 4%.

Table 1 below lists exemplary embodiments of reaction solutions disclosed herein.

TABLE 1

Exemplary embodiments of reaction solutions 110

| Component | Embodiment 1 | Embodiment 2 | Embodiment 3 | Embodiment 4 |
|---|---|---|---|---|
| [dATP], [dTTP] (μM) | 1000, 1000 | 1000, 1000 | 2000, 2000 | 2000, 2000 |
| [dGTP], [dCTP] (μM) | 50, 50 | 50, 50 | 50, 50 | 100, 100 |
| $Mg^{2+}$ | 2.5 | 2 | 4 | 4 |
| Betaine (M) | 0 or 1 | 0 or 1 | 0 or 1 | 0 or 1 |
| DMSO (%) | 0 or 1 | 0 or 1 | 0 or 1 | 0 or 1 |

In some cases, the reaction solution comprises one or more labels suitable for labeling a reaction product. In some embodiments, one or more labels are covalently attached to one or more primers. In some embodiments, a primer comprises a covalently attached label. In some embodiments, one or more labels are covalently attached to one or more nucleotide triphosphates. In some embodiments, a nucleotide triphosphate comprises a covalently attached label. Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniques, Academic Press, San Diego (1992) and Garman A., Non-Radioactive Labeling, Academic Press (1997)).

In some embodiments, a fluorophore is used as a label. Fluorophores useful as labels include, but are not limited to, fluoresceins (see, e.g., U.S. Pat. Nos. 5,188,934, 6,008,379, and 6,020,481), rhodamines (see, e.g., U.S. Pat. Nos. 5,366,860, 5,847,162, 5,936,087, 6,051,719, and 6,191,278), benzophenoxazines (see, e.g., U.S. Pat. No. 6,140,500), coumarins, energy-transfer fluorescent dyes, comprising pairs of donors and acceptors (see, e.g., U.S. Pat. Nos. 5,863,727; 5,800,996; and 5,945,526), cyanines (see, e.g., WO 9745539), lissamines, phycoerythrins, pyrenyloxytrisulfonic acid-based fluorophores (e.g., Cascade Blue®), and any derivatives thereof. Examples of fluorescein dyes include, but are not limited to, Fluorescein Isothiocyanate ("FITC"); 6-carboxyfluorescein ("FAM"); 5-Tetrachloro-Fluorescein, ("TET"); 2',4',1,4-tetrachlorofluorescein; 2',4',5',7',1,4-hexachlorofluorescein; 6-carboxy-2',4,4',5',7,7'-hexachlorofluorescein ("HEX"); fluorinated analogs of fluorescein (such as Oregon Green® 488, Oregon Green® 500, and Oregon Green® 514); and 6-carboxy-4',5'-dichloro-2',7'-dimethoxyfluorescein ("JOE"). Exemplary cyanine dyes include, without limitation, Cy2, Cy3, Cy3.5, Cy5, Cy5.5, Cy7, and the WellRed® infrared dyes D1, D2, D3 and D4. Exemplary rhodamine dyes include, e.g., Rhodamine Green, Rhodamine Red, Tetramethylrhodamine, carboxytetramethylrhodamine ("TAMRA"), sulforhodamine 101 acid chloride (Texas Red), and carboxy-X-rhodamine ("ROX"). Exemplary coumarin dyes include, e.g., 6,8-Difluoro-7-hydroxycoumarin-3-carboxylic acid (Pacific Blue™) and aminomethylcoumarin acetate ("AMCA"). Additional labels can be derived from, e.g., FluorX (Amersham). Fluorophores can include Alexa Fluor® dyes (e.g., sulfonated versions of dye molecules such as, without limitation, fluorescein, rhodamine, cyanine, coumarin, and the like). Exemplary Alexa Fluor® dyes include, e.g., Alexa 350, Alexa 430, Alexa 430, Alexa 488, Alexa 532, Alexa 546, Alexa 568, and Alexa 594. Fluorophores can include BODIPY™ dyes (comprising the core structure 4,4-difluoro-4-bora-3a,4a-diaza-s-indacene), such as, e.g., BODIPY 630/650, BODIPY 650/665, BODIPY-FL, BODIPY-R6G, BODIPY-TMR, BODIPY-TRX. In certain aspects, the fluorescent label is selected from fluorescent labels that are compatible with CE analysis such as FAM, TET, ROX, NED™, VIC™, or JOE.

In some embodiments, the label is a radioactive label. The radioactive label can be $^{32}P$. The radioactive label can be $^{33}P$. The radioactive label can be $^{35}S$. In some embodiments, the label is an electrochemical label. The electrochemical label can be ferrocene. In some embodiments, the label is an affinity label. The affinity label can be biotin. The affinity label can be digoxygenin.

The reaction solution can comprise more than one label. In some embodiments, the reaction solution comprises different fluorophores capable of emitting light at different, spectrally-resolvable wavelengths (e.g., 4 differently colored fluorophores); certain such labeled probes are known in the art and described above, and in U.S. Pat. No. 6,140,054. A dual labeled fluorescent probe that includes a reporter fluorophore and a quencher fluorophore is used in some embodiments. Other examples can include Freedom® dyes that are commercially available surrogates for common dyes. It will be appreciated that pairs of fluorophores can be chosen to have distinct emission spectra so that they can be easily distinguished.

The reaction 120 (see FIG. 1A) can comprise a nucleic acid synthesis step. The nucleic acid synthesis step can comprise annealing the one or more primers 116 to a nucleic acid template. The nucleic acid synthesis step can further comprise polymerase-mediated extension of the one or more primers 116 along the template. In some embodiments, the one or more primers 116 are extended into a locus of interest. In some embodiments, the one or more primers 116 are extended within a locus of interest. In some embodiments, the one or more primers 116 are extended across a locus of interest. Exemplary loci are described herein. In some cases, the reaction 120 generates reaction products which are subjected to analysis 130. For example, polymerase-mediated extension of the one or more primers 116 can generate extension products which are subjected to analysis 130.

The reaction 120 can comprise an amplification reaction. The amplification reaction can generate amplification products (e.g., amplicons). The amplification products can be subjected to analysis 130. Examples of amplification reactions include, without limitation, PCR, NASBA (nucleic acid sequence based amplification), SDA (strand displacement amplification), LAMP (loop-mediated isothermal amplification), and RCA (rolling circle amplification). See, e.g., U.S. Pat. No. 4,683,202 (PCR); U.S. Pat. No. 6,326,173 and *Journal of Virological Methods* 151:283-293 (2008) (NASBA); U.S. Pat. No. 5,648,211 (SDA); U.S. Pat. No. 6,410,278 (LAMP); and U.S. Pat. No. 6,287,824 (RCA). All of the foregoing are incorporated herein by reference. The skilled artisan will understand what reagents are appropriate to provide. Each of these methods involves DNA synthesis, and as such involves the use of DNA polymerases, nucleotides, and divalent cations (supplied as a salt), particularly magnesium, in a solution conducive to DNA polymerization and in which the template is present. The methods can vary in terms of providing additional catalytic activities, the use of thermocycling or isothermal incubation, and the use and structure of primers. A buffer at a suitable pH is also typically provided. In some embodiments, the suitable pH ranges from about 7 to about 8. In some embodiments, the suitable pH ranges from about 6.5 to about 8.5. In some embodiments, the suitable pH ranges from about 6 to about 9. In some embodiments, the suitable pH ranges from about 7.4 to about 7.5.

In some cases, the reaction 120 comprises PCR. PCR can comprise repeated rounds of amplification. A "round" or "cycle" of amplification can comprise a denaturation step, a primer annealing step, and a polymerase-mediated extension step. The reaction can be thermocycled so as to drive denaturation of nucleic acids in a high temperature step, annealing of the primers to templates at a lower temperature step, and extension at a temperature which can be but is not necessarily higher than that of the annealing step. In some cases, the PCR comprises an annealing step at a temperature at or below 75° C. In some cases, the PCR comprises an annealing step at a temperature at or below 70° C. In some cases, the PCR comprises an annealing step at a temperature at or below 65° C. In some cases, the PCR comprises an annealing step at a temperature that ranges from about 50° C. to about 75° C. In some cases, the PCR comprises an annealing step at a temperature that ranges from about 57° C. and about 63° C. In some cases, the PCR comprises an annealing step at a temperature that ranges from about 52° C. and about 58° C. In some cases, the PCR comprises an annealing step at a temperature that ranges from about 62° C. and about 68° C. Amplification can proceed as the amplification products of one cycle can serve as template in the next cycle. Amplification can proceed in a linear or exponential fashion. In linear PCR, the reaction mixture can comprise one or more forward primers to be extended into, within, or across a region of interest. In exponential PCR, the reaction mixture can comprise forward and reverse primers which flank a region of interest. In some embodiments, a touchdown annealing procedure is used. In a touchdown annealing procedure, a first annealing temperature is used in an early cycle, such as the first cycle, and a second annealing temperature, lower than the first annealing temperature, is used a later cycle later than the early cycle. The touchdown annealing procedure can comprise using a lower annealing temperature than in the previous cycle in one or more cycles. The touchdown annealing procedure can comprise using a lower annealing temperature than in the previous cycle in 1 to 20 cycles. The touchdown annealing procedure can comprise using a lower annealing temperature than in the previous cycle in 1 to 15 cycles. The touchdown annealing procedure can comprise using a lower annealing temperature than in the previous cycle in 1 to 10 cycles. The touchdown annealing procedure can comprise using a lower annealing temperature than in the previous cycle in 5 to 20 cycles. The touchdown annealing procedure can comprise using a lower annealing temperature than in the previous cycle in 5 to 15 cycles. The touchdown annealing procedure can comprise using a lower annealing temperature than in the previous cycle in 5 to 10 cycles. The touchdown annealing procedure can comprise using a lower annealing temperature than in the previous cycle in 10 to 20 cycles. The touchdown annealing procedure can comprise using a lower annealing temperature than in the previous cycle in 10 to 15 cycles. In some embodiments, the touchdown annealing procedure comprises a cycle with a first annealing temperature ranging from about 58° C. to about 72° C. In some embodiments, the touchdown annealing procedure comprises a cycle with a first annealing temperature ranging from about 60° C. to about 70° C. In some embodiments, the touchdown annealing procedure comprises a cycle with a first annealing temperature ranging from about 62° C. to about 68° C. In some embodiments, the touchdown annealing procedure comprises a cycle with a first annealing temperature ranging from about 64° C. to about 66° C. In some embodiments, the touchdown annealing procedure comprises a cycle with a second annealing temperature ranging from about 48° C. to about 62° C. In some embodiments, the touchdown annealing procedure comprises a cycle with a second annealing temperature ranging from about 50° C. to about 60° C. In some embodiments, the touchdown annealing procedure comprises a cycle with a second annealing temperature ranging from about 52° C. to about 58° C. In some embodiments, the touchdown annealing procedure comprises a cycle with a second annealing temperature ranging from about 54° C. to about 56° C. The second annealing temperature can be lower than the first annealing temperature. The second annealing temperature can be used in a cycle later that the cycle in which the first annealing temperature is used, such as 1, 2, 3, 4, 5, 6, 7, 8, 9, 10, 11, 12, 13, 14, 15, 16, 17, 18, 19, or 20 cycles after the cycle in which the first annealing temperature is used. When the second annealing temperature is used in a cycle more than one cycle after the first annealing temperature is used, the annealing temperatures in the intervening cycle or cycles can be about the same as the first annealing temperature. Alternatively, the annealing temperatures in the intervening cycle or cycles can be about the same as the second annealing temperature. Alternatively, the annealing temperatures in the intervening cycle or cycles can be or between the first and the second annealing temperature. For example, the annealing temperature in an intervening cycle or cycles can decrease linearly. The rate of linear decrease can range from, e.g., 0.2° C. per cycle to 10° C. per cycle. The rate of linear decrease can range from 0.5° C. per cycle to 5° C. per cycle. The rate of linear decrease can range from 0.5° C. per cycle to 3° C. per cycle. The rate of linear decrease can range from 0.5° C. per cycle to 2° C. per cycle. The rate of linear decrease can range from 0.5° C. per cycle to 1.5° C. per cycle. The rate of linear decrease can range from 0.7° C. per cycle to 1.3° C. per cycle.

The reaction 120 can comprise between about 1 to about 40 amplification cycles. For example, the reaction 120 can comprise between about 10 to about 40 cycles. For example, the reaction 120 can comprise between about 15 to about 35 cycles. The reaction 120 can comprise about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 amplification cycles. In some cases, the reaction 120 comprises no more than 35 amplification cycles. In some cases, the reaction 120 comprises no more than 30 amplification cycles. In some cases, the reaction 120 comprises no more than 25 amplification cycles.

In NASBA, an RNA polymerase (RNAP) is provided in addition to the DNA polymerase, which can also be a reverse transcriptase (RT) (e.g., an enzyme that can catalyze DNA synthesis using either an RNA or DNA template). Primers can be provided that are similar to those used in PCR except that at least one primer can additionally comprise a promoter sequence that is recognized by the RNAP. Thus, the product of the RT serves as template for the RNAP, which synthesizes RNA that serves as template for the RT, leading to amplification. In some forms of NASBA, RNase H is provided to produce single-stranded DNA after synthesis of an RNA-DNA hybrid by RT. Amplification occurs via the combined action of the RT and RNAP, in the absence of repeated thermal denaturation.

SDA is a technique in which DNA is amplified in an isothermal and asynchronous manner, meaning that cyclic thermal denaturation is not used to separate the strands;

instead, strand displacement occurs through DNA synthesis itself, wherein extension of a 3' OH causes displacement of the downstream strand. The 3' OH is provided initially by an exterior primer and subsequently by a nicking reaction. Two pairs of primers can be provided. One 'interior' pair binds surrounding the amplicon and additionally comprises 5' flaps containing a restriction site. The other, 'exterior' pair is positioned distally, i.e., further from the target region. An interior primer can bind the template, be extended, and then be displaced by synthesis from the corresponding exterior primer. Subsequently, the displaced DNA is made double-stranded, e.g., by second strand synthesis. The next step is to nick one strand of the double stranded molecule, which can be done by using modified nucleotides and a restriction site wherein the cleavage site is inactivated on one strand (but not the other) by the modified nucleotide. The restriction enzyme corresponding to this site is provided in the reaction and generates the nick. The 3' OH at the resulting nick is then extended by the DNA polymerase, displacing one strand (which can again serve as a template) and the regenerated double strand molecule is again a substrate for nicking followed by extension and displacement, leading to amplification. Repeated thermal denaturation is not necessary.

LAMP is an amplification procedure designed to be highly specific, that is, it can discriminate between templates differing by only a single nucleotide polymorphism (SNP), in that one allele is a substrate for amplification and the other is not. It is also isothermal. As in SDA, two pairs of primers, interior and exterior, can be provided; the interior primers can also have a 5' flap. However, in LAMP, the 5' flap of each interior primer contains a sequence matching a sequence within the template strand to which it binds, interior to the site where the 3' portion of the primer binds. For example, if the primer anneals to the (+) strand of a template molecule, which contains the downstream sequence A, then the primer flap can also contain sequence A. Notably, the SNP locus which is to be discriminated by this reaction is located at the edge of the region bound by the flap, corresponding to the last base at the 5' end of the flap. The last base at the 5' end of the reverse interior primer flap also corresponds to the SNP locus. As in SDA, the interior primer is extended and then displaced by extension of the exterior primer. When this occurs, the 5' flap forms a loop by binding its complement (which is now part of the same molecule; continuing the above example, the displaced strand contains the reverse complement of sequence A, designated sequence T, and the sequence A in the flap binds intramolecularly to sequence T). The reverse interior primer anneals to the looped displaced strand, interior to its 3' end (which corresponds to the reverse exterior primer) and primes synthesis, which displaces the loop and forms a partially double-stranded, partially single stranded DNA. Then, a reverse exterior primer anneals to the single stranded portion and primes synthesis, causing strand displacement. The displaced strand can now form a loop wherein its 3' end is paired to an internal portion of the molecule. Only if the SNP locus matches the 3' end (which is derived from an interior primer flap that was exogenously supplied) does extension occur. Further primer annealing, looping, and extension/displacement events, described in the reference cited above, result in selective amplification of templates with the SNP allele matching the primer flap.

In RCA, a circular DNA template is used. A primer anneals to the circle and is extended continuously, with the polymerase displacing the DNA synthesized during the previous revolution as it proceeds. This reaction proceeds with linear kinetics and produces long, concatemerized products. In double-primed RCA, a second primer is provided that anneals to the concatemerized product of the above reaction. This version of the reaction allows use of product as template, and therefore results in exponential kinetics. As in other isothermal reactions, product is made suitable for annealing to primer in double-primed RCA through strand displacement due to extension of upstream primers; in this case the primers can be bound to other concatemers further upstream in the template strand.

Reaction products generated by a reaction 120 can be subjected to analysis 130 (see FIG. 1A). The analysis can be useful for assessment of genomic regions comprising repeating A/T rich segments and homopolymeric segments, such as homopolymeric segments of A, T, or U residues, which can be consecutive or interrupted once by one to three other nucleotides.

In some cases, the analysis comprises determining a sequence of a reaction product. The term "determining a sequence" as used herein refers to a method by which the identities of at least 8 consecutive nucleotides of a polynucleotide are obtained. In some embodiments, the identities of at least 10 consecutive nucleotides of a polynucleotide are obtained. In some embodiments, the identities of at least 12 consecutive nucleotides of a polynucleotide are obtained. In some embodiments, the identities of at least 16 consecutive nucleotides of a polynucleotide are obtained. In some embodiments, the sequence of a homopolymeric segment is determined by comparing capillary electrophoresis data for an amplification reaction product generated from a sample comprising the homopolymeric segment. The capillary electrophoresis data can be interpreted by comparing it to calibration data from one or more standards. The one or more standards can comprise one or more amplification reaction products generated from a reference sample. The reference sample can comprise a nucleic acid having a known sequence. The reference sample can comprise an artificially synthesized nucleic acid. The reference sample can comprise a nucleic acid containing a homopolymeric segment of a known length. Sequencing methods can comprise a sequencing reaction that creates or modifies nucleic acid molecules artificially so as to make them detectable, thereby allowing sequence determination. Sequencing methods can comprise using a sequencing apparatus which can detect a nucleic acid molecule in an electromagnetic manner, e.g., based on electromagnetic radiation (e.g., fluorescent or radioactive emission) or electromagnetic field effects (as in, e.g., nanopore sequencing). Sequencing methods suitable for analysis of reaction products described herein can include Sanger sequencing or next-generation sequencing. Next generation sequencing can involve sequencing of clonally amplified DNA templates or single DNA molecules in a massively parallel fashion. Exemplary sequencing methods include, but are not limited to, sequencing-by-synthesis, ion pyrosequencing, reversible dye terminator sequencing, semiconductor sequencing, sequencing by ligation, single-molecule sequencing, sequencing by hybridization, and nanopore sequencing. Platforms for sequencing by synthesis can include those available from Illumina, 454 Life Sciences, Helicos Biosciences, Thermo Fisher/Ion Torrent (e.g., Personal Genome Machine, Proton), and Oxford Nanopore (eg, MinION) and Qiagen. Exemplary Illumina platforms are described in Gudmundsson et al (Nat. Genet. 2009 41:1122-6), Out et al (Hum. Mutat. 2009 30:1703-12) and Turner (Nat. Methods 2009 6:315-6), U.S. Patent Application Publication No. US20080160580, U.S. Pat. Nos. 6,306,597 and 7,115,400. Exemplary Helicos Biosciences platforms include the True Single Molecule Sequencing platform. Exemplary platforms for ion semiconductor sequencing are described in U.S. Pat. No. 7,948,015 and include, e.g., the Ion Torrent Personal Genome Machine (PGM). Exemplary platforms for pyrosequencing are described in U.S. Pat. Nos. 7,211,390; 7,244,559; and 7,264,929, and can include the GS Flex. Exemplary platforms for sequencing by ligation are described in U.S. Pat. No. 5,750,341 and include, e.g., the SOLiD sequencing platform. Exemplary platforms for single-molecule sequencing include the Helicos True Single Molecule Sequencing platform and the SMRT® system from Pacific Biosciences. In some cases, extension products are subjected to nucleic acid sequencing, without requiring amplification prior to sequencing. For example, sequencing by, e.g., the SMRT® system by Pacific Biosciences can comprise sequencing an extension product described herein as it is being synthesized.

In some cases, analysis 130 comprises size analysis. Size analysis can comprise determining the size of one or more reaction products generated by a method described herein. Size analysis can comprise determining an amount of reaction products having a certain size.

Size analysis can comprise an electrophoresis method. Exemplary electrophoresis methods include, e.g., gel electrophoresis and capillary electrophoresis (CE). In some cases, size analysis comprises CE analysis. CE analysis can comprise use of instrumentation such as the ABI 3100, 3130, 3730, or 3500 models. Other implementations include any instrument capable of electrophoretic sizing of DNA and multicolor resolution. For example, the Beckman Vidiera or SEQ6000 capillary electrophoresis systems for the detection of WellRed infrared dyes (D1, D2, D3 and D4) can also be used, or the Li-Cor instrument incorporating IRDyes. Other methods that can be used include microfluidic CE systems such as the Agilent 2100 Bioanalyzer and similar platforms, mass spectrometry, agarose gel electrophoresis followed by scan densitometry, and analysis of radiolabeled products using phosphorImager or scan densitometry of autoradiographs. In some cases, size analysis comprises assessing intensities of peaks observed in CE electropherograms, phosphorimager scans, densitometric scans, mass spectra, or other forms of data. Size analysis can comprise determination of peak height, area under the curve (integration), or curve fitting. In some embodiments, size analysis comprises comparing data from a sample to data from one or more standards with one or more repeating nucleotide segments of known length. In some embodiments, size analysis comprises comparing data from a sample to data from one or more standards with one or more repeating A/T rich segments or homopolymeric nucleotide segments of known length. The comparison can comprise regression analysis. An example of using of standards with similar AT/GC content to extrapolate a length of a nucleic acid segment is provided in Filipovic-Sadic S, et al., "A novel FMR1 PCR method for the routine detection of low abundance expanded alleles and full mutations in fragile X syndrome," Clin Chem. 2010 March; 56(3):399-408 (doi: 10.1373/clinchem.2009.136101, Epub 2010 Jan. 7). This approach can be adapted for use with repeating A/T rich segments or homopolymeric segments, among others.

Methods described herein can be used to determine a length of a repeating A/T rich segment or homopolymeric segment, such as a homopolymeric segment of A, T, or U residues, which can be consecutive or interrupted once by one to three other nucleotides.

Methods described herein can detect a repeating A/T rich segment or homopolymeric segment above 10 nucleotides in length, which can be consecutive or interrupted once by one to three other nucleotides. For example, methods described herein can detect A- or T-homopolymeric segments or repeating A/T rich segments that are above 8, above 9, above 10, above 11, above 12, above 13, above 14, above 15, above 16, above 17, above 18, above 19, above 20, above 21, above 22, above 23, above 24, above 25, above 26, above 27, above 28, above 29, above 30, above 31, above 32, above 33, above 34, above 35, above 36, above 37, above 38, above 39, above 40, above 41, above 42, above 43, above 44, above 45, above 46, above 47, above 48, above 49, above 50, above 51, above 52, above 53, above 54, above 55, above 56, above 57, above 58, above 59, or above 60 nucleotides in length. Methods described herein can detect A- or T-homopolymeric segments or repeating A/T rich segments that range from about 10 to about 40 nucleotides in length. Methods described herein can detect A- or T-homopolymeric segments or repeating A/T rich segments that range from about 10 to about 50 nucleotides in length. Methods described herein can detect A- or T-homopolymeric segments or repeating A/T rich segments that range from about 10 to about 48 nucleotides in length. Methods described herein can detect A- or T-homopolymeric segments or repeating A/T rich segments that range from about 10 to about 60 nucleotides in length. Methods described herein can detect A- or T-homopolymeric segments or repeating A/T rich segments that range from about 8 to about 60 nucleotides in length. Methods described herein can detect A- or T-homopolymeric segments or repeating A/T rich segments that range from about 15 to about 40 nucleotides in length. Methods described herein can detect A- or T-homopolymeric segments or repeating A/T rich segments that range from about 20 to about 40 nucleotides in length. Methods described herein can detect A- or T-homopolymeric segments or repeating A/T rich segments that range from about 30 to about 40 nucleotides in length. Methods described herein can detect A- or T-homopolymeric segments or repeating A/T rich segments that range from about 15 to about 50 nucleotides in length. Methods described herein can detect A- or T-homopolymeric segments or repeating A/T rich segments that range from about 20 to about 50 nucleotides in length. Methods described herein can detect A- or T-homopolymeric segments or repeating A/T rich segments that range from about 30 to about 50 nucleotides in length. Methods described herein can detect A- or T-homopolymeric segments or repeating A/T rich segments that range from about 15 to about 48 nucleotides in length. Methods described herein can detect A- or T-homopolymeric segments or repeating A/T rich segments that range from about 20 to about 48 nucleotides in length. Methods described herein can detect A- or T-homopolymeric segments or repeating A/T rich segments that range from about 30 to about 48 nucleotides in length. Methods described herein can detect A- or T-homopolymeric segments or repeating A/T rich segments that range from about 15 to about 60 nucleotides in length. Methods described herein can detect A- or T-homopolymeric segments or repeating A/T rich segments that range from about 20 to about 60 nucleotides in length. Methods described herein can detect A- or T-homopolymeric segments or repeating A/T rich segments that range from about 30 to about 60 nucleotides in length.

Methods described herein can be used to detect and distinguish a plurality of repeat length polymorphisms in a single sample or across a plurality of samples. For example, methods described herein can distinguish amplicons containing A- or T-homopolymeric segments or repeating A/T rich segments that are below 20 nucleotides in length, between 20 and 29 nucleotides in length, and 30 or more nucleotides in length. In some cases, methods described herein can distinguish amplicons containing A- or T-homopolymeric segments or repeating A/T rich segments that differ in size by 1 nucleotide. In some cases, methods described herein can distinguish amplicons containing A- or T-homopolymeric segments or repeating A/T rich segments that differ in size by 2 nucleotides or less. In some cases, methods described herein can distinguish amplicons containing A- or T-homopolymeric segments or repeating A/T rich segments that differ in size by 3 nucleotides or less. In some cases, methods described herein can distinguish amplicons containing A- or T-homopolymeric segments or repeating A/T rich segments that differ in size by 4 nucleotides or less. In some cases, methods described herein can distinguish amplicons containing A- or T-homopolymeric segments or repeating A/T rich segments that differ in size by 5 nucleotides or less. In some cases, methods described herein can distinguish amplicons containing A- or T-homopolymeric segments or repeating A/T rich segments that differ in size by 6 nucleotides or less. In some cases, methods described herein can distinguish amplicons containing A- or T-homopolymeric segments or repeating A/T rich segments that differ in size by 7 nucleotides or less. In some cases, methods described herein can distinguish amplicons containing A- or T-homopolymeric segments or repeating A/T rich segments that differ in size by 8 nucleotides or less. In some cases, methods described herein can distinguish amplicons containing A- or T-homopolymeric segments or repeating A/T rich segments that differ in size by 9 nucleotides or less. In some cases, methods described herein can distinguish amplicons containing A- or T-homopolymeric segments or repeating A/T rich segments that differ in size by 10 nucleotides or less. In some embodiments, the methods described herein can distinguish amplicons containing A- or T-homopolymeric segments or repeating A/T rich segments that are at least 20 nucleotides long and that differ in size by a number of nucleotides as discussed above. In some embodiments, methods described herein can distinguish amplicons containing A- or T-homopolymeric segments or repeating A/T rich segments that are at least 30 nucleotides long and that differ in size by a number of nucleotides as discussed above.

In some cases, methods described herein are capable of distinguishing a first sample comprising a first template with a homopolymeric segment of length (n+1) and a second template with a homopolymeric segment of length (n−1) from a sample comprising a template with a homopolymeric segment of length (n), wherein n is greater than about 20 and less than about 40. In some cases, n is greater than about 30 and less than about 40. In some cases, n is greater than about 35 and less than about 40. In some cases, methods described herein are capable of distinguishing a first sample comprising a first template with a repeating A/T rich segment of length (n+1) and a second template with a repeating A/T rich segment of length (n−1) from a sample comprising a template with a repeating A/T rich segment of length (n), wherein n is greater than about 20 and less than about 40. In some cases, n is greater than about 30 and less than about 40. In some cases, n is greater than about 35 and less than about 40.

Figure 2:
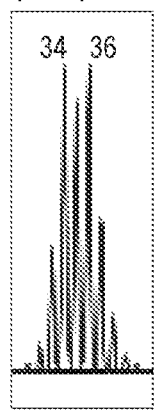
FIG. 2 depicts an exemplary desired capillary electrophoresis (CE) peak profile and an exemplary undesired CE peak profile for two alleles with similar repeat numbers.
Figure 2:
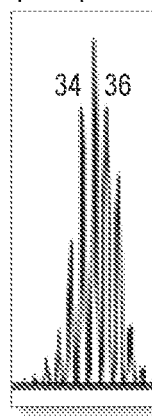

For example, methods described herein can be capable of distinguishing a first sample comprising true 34T and 36T alleles of an rs10524523 locus from a sample comprising non-target 35T segments which result from polymerase slippage/stutter. FIG. 2 depicts an exemplary desired peak profile from CE analysis of a sample known to be heterozygous for the 34T/36T alleles. In a desired peak profile, one or both of the 34T and 36T peaks have a greater intensity than the intensity of a non-target 35T peak. By contrast, in an exemplary undesired peak profile, a non-target 35T peak intensity is higher than intensity of the 34T and 36T peaks.

Disclosed herein are kits useful for performing one or more methods described herein. A kit can comprise NTPs, such as dNTPs, having an AT/GC ratio greater than 2. A kit can include individual aliquots of NTPs and instructions for preparing a reaction solution comprising NTPs as described herein. A kit can further comprise a primer suitable for extension into, within, or across a homopolymeric segment of at least 10 consecutive A or T residues. A kit can further comprise a primer suitable for extension into, within, or across a repeating A/T rich segment of at least 10 consecutive A or T residues. In some cases, a kit comprises at least two primers. The primers can be suitable for amplifying a genetic locus comprising a homopolymeric segment of at least 10 consecutive A residues or at least 10 consecutive T residues. In some cases, the homopolymeric segment is the rs10524523 polymorphism of the TOMM40 gene. In some cases, a kit comprises at least one primer that hybridizes upstream of the rs10524523 polymorphism of the TOMM40 gene. In some cases, a kit comprises a second primer that hybridizes downstream of the rs10524523 polymorphism of the TOMM40 gene. In some cases, the AT/GC ratio has a value described herein, such as a value that ranges from about 10 to about 40 or a value that ranges from about 15 and about 30. In some cases, a kit further comprises a polymerase, which can be a polymerase described herein. In some cases, a kit further comprises magnesium in a molar amount in a range disclosed herein, e.g., in the range from about 80% to about 150% of the molar amount of total NTPs. In some embodiments, a kit further comprises a magnesium stock solution. In some embodiments, a kit further comprises a solution comprising magnesium in a concentration of about 10 mM to about 2.5 M. In some embodiments, a kit further comprises a solution comprising magnesium in a concentration of about 10 mM to about 3 M. In some cases, a kit further comprises one or more additives, which can be one or more additives described herein. Exemplary additives are described herein. In some cases, a kit further comprises betaine. In some cases, a kit further comprises a betaine analog. In some cases, a kit further comprises DMSO. In some cases, a kit further comprises betaine and DMSO.

A kit can include reference standards. The reference standards can comprise one or more repeating A/T-rich segments, such as one or more homopolymeric segments, of known lengths. Exemplary homopolymeric segments are described herein.

A kit can include a packaging material. As used herein, the term "packaging material" can refer to a physical structure housing the components of the kit. The packaging material can maintain sterility of the kit components, and can be made of material commonly used for such purposes (e.g., paper, corrugated fiber, glass, plastic, foil, ampules, etc.). A kit can also include a buffering agent, a preservative, or a protein/nucleic acid stabilizing agent.

Methods and kits described herein can have many applications. For example, methods described herein can be useful in disease diagnosis, disease prediction, selection of a therapeutic regimen, genotyping, identification, forensics, nucleic acid profiling, kinship analysis, genetic linkage analysis, marker-assisted selection, assessment of gene regulation, population genetics, and taxonomic studies, among others.

Methods and kits described herein can be useful for of detecting a genotype associated with late-onset Alzheimer's disease. For example, methods described herein can be useful for genotyping a rs10524523 polymorphism of the TOMM40 gene.

EXAMPLES

The following examples illustrate various embodiments and are not intended to limit the scope of the invention.

Example 1. Effect of Biased dNTP Ratios on Polymerase Slippage/Stuttering

Heterozygous DNA samples, each containing two known poly-T repeat lengths for the TOMM40 poly-T polymorphism, were provided as described in Table 2.

TABLE 2

Sample names and poly-T repeat lengths.

| Sample Name | rs10524523 Repeat length genotype (nt/nt) |
|---|---|
| RS1310 | 35/36 |
| RS1311 | 16/36 |
| RS1319 | 34/36 |

10 ng of sample DNA were amplified using Phoenix Taq (Enzymatics) in a PCR reaction mixture comprising 1× Phoenix buffer and 2.5 mM Mg2+. The primers were /56-FAM/CCAAAGCATTGGGATTACTGGC (SEQ ID NO: 1) (Forward) and GATTGCTTGAGCCTAGGCATTC (SEQ ID NO: 2) (Reverse). The following final concentrations of dNTPs were used in the reactions: 250 μM each dNTP; 100 μM each of dATP and dTTP with 50 μM each of dCTP and dGTP ("100/50" AT/GC ratio); 250 μM each of dATP and dTTP with 50 μM each of dCTP and dGTP ("250/50"), 500 μM each of dATP and dTTP with 50 μM each of dCTP and dGTP ("500/50"), and 1000 μM each of dATP and dTTP with 50 μM each of dCTP and dGTP ("1000/50"). PCR was conducted for 35 cycles and the crude product was diluted 100-fold prior to capillary electrophoresis (CE) analysis. CE analysis was performed on an ABI 3500xL. PCR products were injected at 2.5 kv for 20 seconds. ROX 400HD was used as ladder. Mobility and correction factor (as described in Filipovic-Sadie et al., 2010, supra) were obtained from standards of known polyT length (8T, 12T, 16T, 20T, 24T, 48T) and extrapolated to determine the genotype of the unknown sample.

FIGS. 3A-3D depict CE peak profiles for each DNA sample listed in Table 2, with the target peaks labeled. Because the poly-T lengths are known for each sample, polymerase slippage/stuttering can be quantified by the number of extra non-target peaks and/or by the ratio of the target peak (N) height to one or more non-target peak heights, such as the height of the N−1 non-target peak. For example, a reduction in the number of non-target peaks (e.g., that exceed a threshold relative to the target or maximum peak) or a higher target peak height as compared to one or more non-target peak heights can be used, separately or together, to assess whether slippage/stuttering is reduced.

Figure 3A:
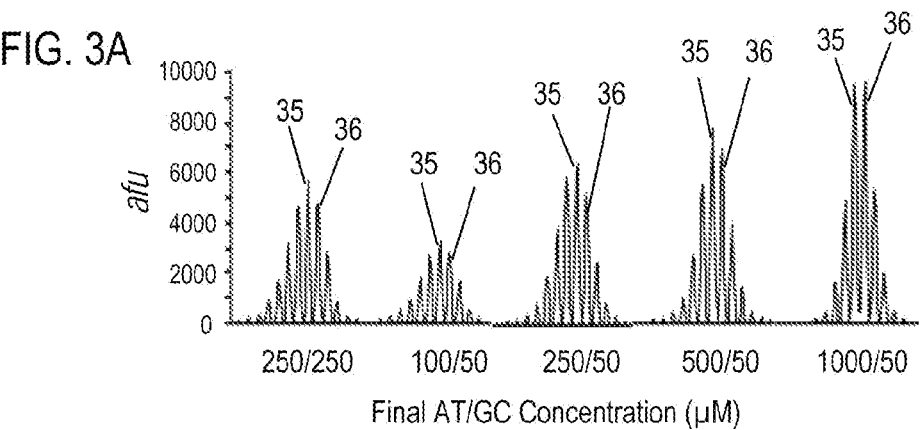
FIG. 3A depicts capillary electrophoresis results from an experiment testing the effect of AT/GC biased ratios on polymerase slippage/stutter, using DNA standard samples containing 35T/36T alleles for the TOMM40 poly-T polymorphism. Information regarding experimental conditions for the data in this and subsequent figures is provided in the Examples section below.

CE peak profiles from the RS1310 samples (35T/36T) are depicted in FIG. 3A. Peak profiles from the RS1310 samples demonstrate that, compared to the non-biased dNTP ratio, there was an increase in the ratios of heights of the 35T and 36T target peaks to non-target peak heights at 250/50 AT/GC. The increase in the peak height ratios for the 35T and 36T target peaks were more pronounced for the 500/50 AT/GC and 1000/50 AT/GC reaction products. For the 1000/50 AT/GC ratio, the heights of the 35T and 36T peaks increased, the heights of the non-target peaks decreased, and fewer non-target peaks were apparent, as compared to the non-biased dNTP ratio of 250/250 AT/GC.

Figure 3B:
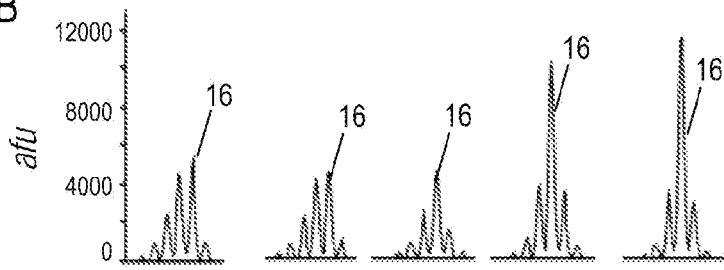
FIG. 3B depicts capillary electrophoresis results from an experiment testing the effect of AT/GC biased ratios on polymerase slippage/stutter, using DNA standard samples containing 16T/36T alleles for the TOMM40 poly-T polymorphism, in the vicinity of the 16T peak.
Figure 3C:
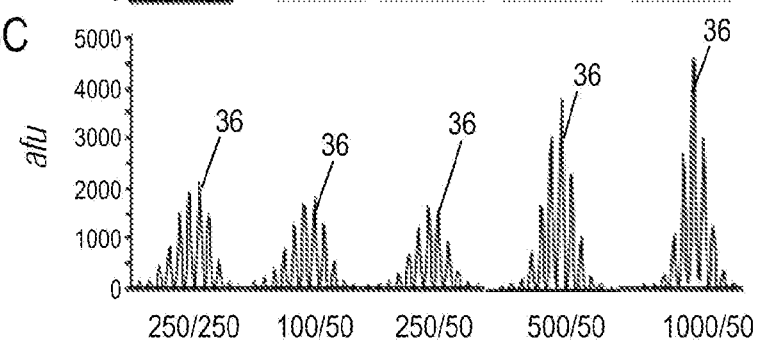
FIG. 3C depicts capillary electrophoresis results from an experiment testing the effect of AT/GC biased ratios on polymerase slippage/stutter, using DNA standard samples containing 16T/36T alleles for the TOMM40 poly-T polymorphism, in the vicinity of the 36T peak.

CE peak profiles from the RS1311 samples (16T/36T) are depicted in FIGS. 3B and 3C. Peak profiles from the RS1311 samples demonstrate that, compared to the non-biased dNTP ratio, the 500/50 and 1000/50 AT/GC reactions products exhibited an increase in the target/non-target peak height ratios for the 16T and 36T target peaks, with the greatest increase apparent for the 1000/50 ratio. There was also a reduction in non-target peak number and intensity relative to the results when the non-biased dNTP ratio of 250/250 AT/GC was used.

Figure 3D:
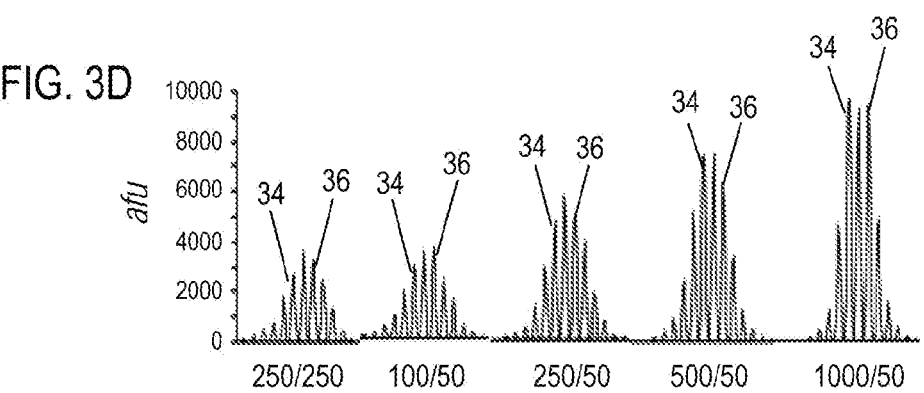
FIG. 3D depicts capillary electrophoresis results from an experiment testing the effect of AT/GC biased ratios on polymerase slippage/stutter, using DNA standard samples containing 34T/36T alleles for the TOMM40 poly-T polymorphism.

CE peak profiles from the RS1319 samples (34T/36T) are depicted in FIG. 3D. The relative height of the non-target 35T peak as compared to target 34T and 36T peak heights can be used to indicate polymerase slippage/stuttering errors, with shorter 35T peak heights generally indicating reduced slippage/stuttering. FIG. 3C demonstrates that the 35T peak was shortest relative to the target 34T and 36T peaks at the 1000/50 AT/GC ratio.

These results, taken together, demonstrate that AT/GC ratios such as, e.g., 250/50, 500/50, and 1000/50 reduced polymerase slippage and stuttering, and improved A or T homopolymer repeat length analysis.

Example 2: Effect of AT/GC Ratios, Mg$^{2+}$ Concentration and Total dNTP Concentration on Polymerase Slippage/Stutter The effects of AT/GC ratio, Mg$^{2+}$ concentration, and total dNTP concentration on polymerase slippage/stuttering were measured by conducting a series of reactions with varying AT/GC concentrations (250/250, 500/500, 1000/1000, 2000/2000, 1000/50, 2000/50, 3000/50, and 2000/100), varying MgSO$_4$ concentration (2, 2.5, 4, 6, 8, and 10 mM), and varying total dNTP concentration (1-8 mM). All reaction mixtures were admixed with 10 ng of RS1319 sample DNA (34T/36T). PCR was conducted for 27 cycles. CE analysis was performed as described in Example 1.

Figure 4:
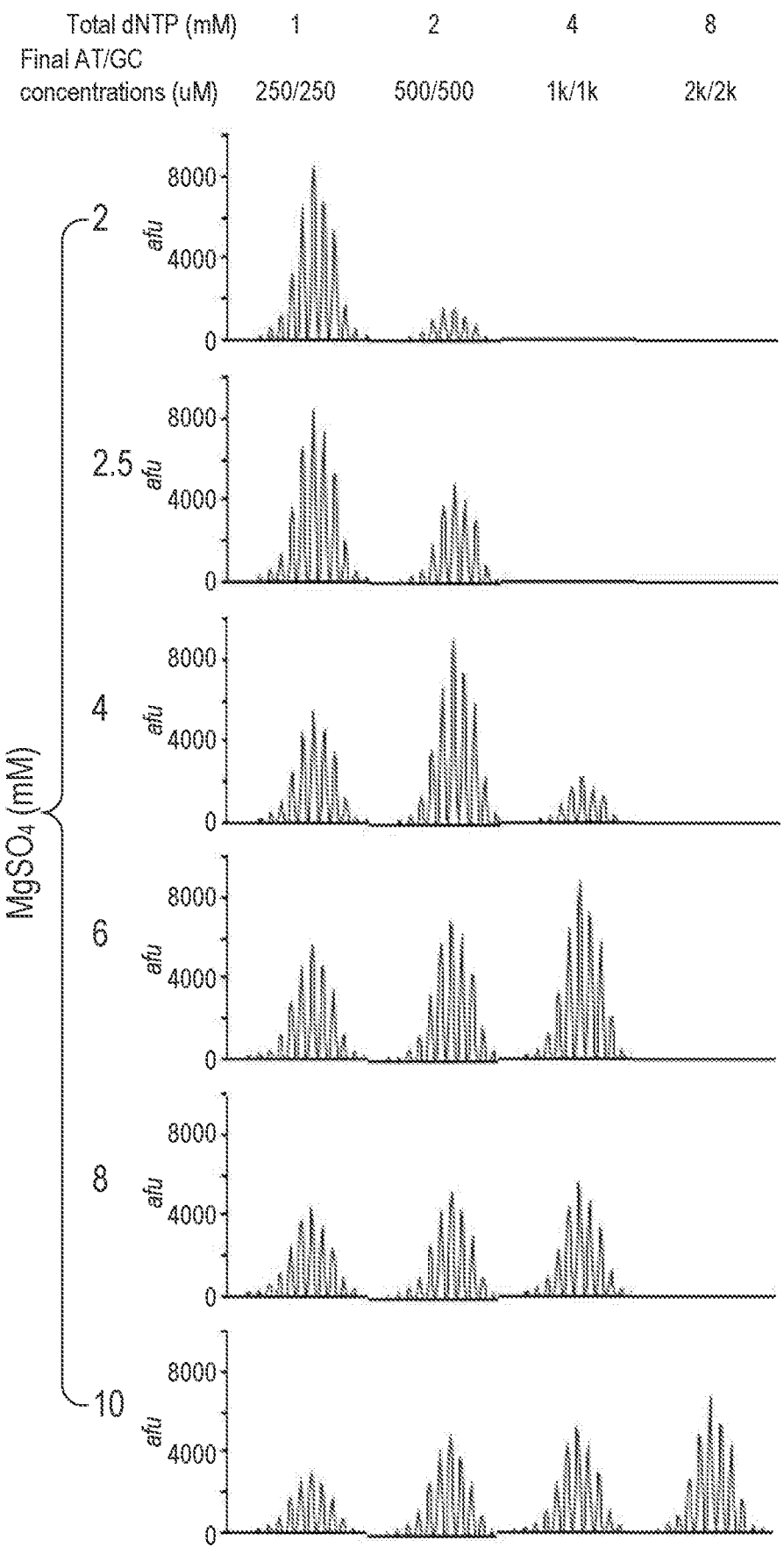
FIG. 4 depicts capillary electrophoresis results from an experiment testing the effects of $Mg^{2+}$ concentration and total dNTP concentration on polymerase slippage/stutter.
Figure 5:
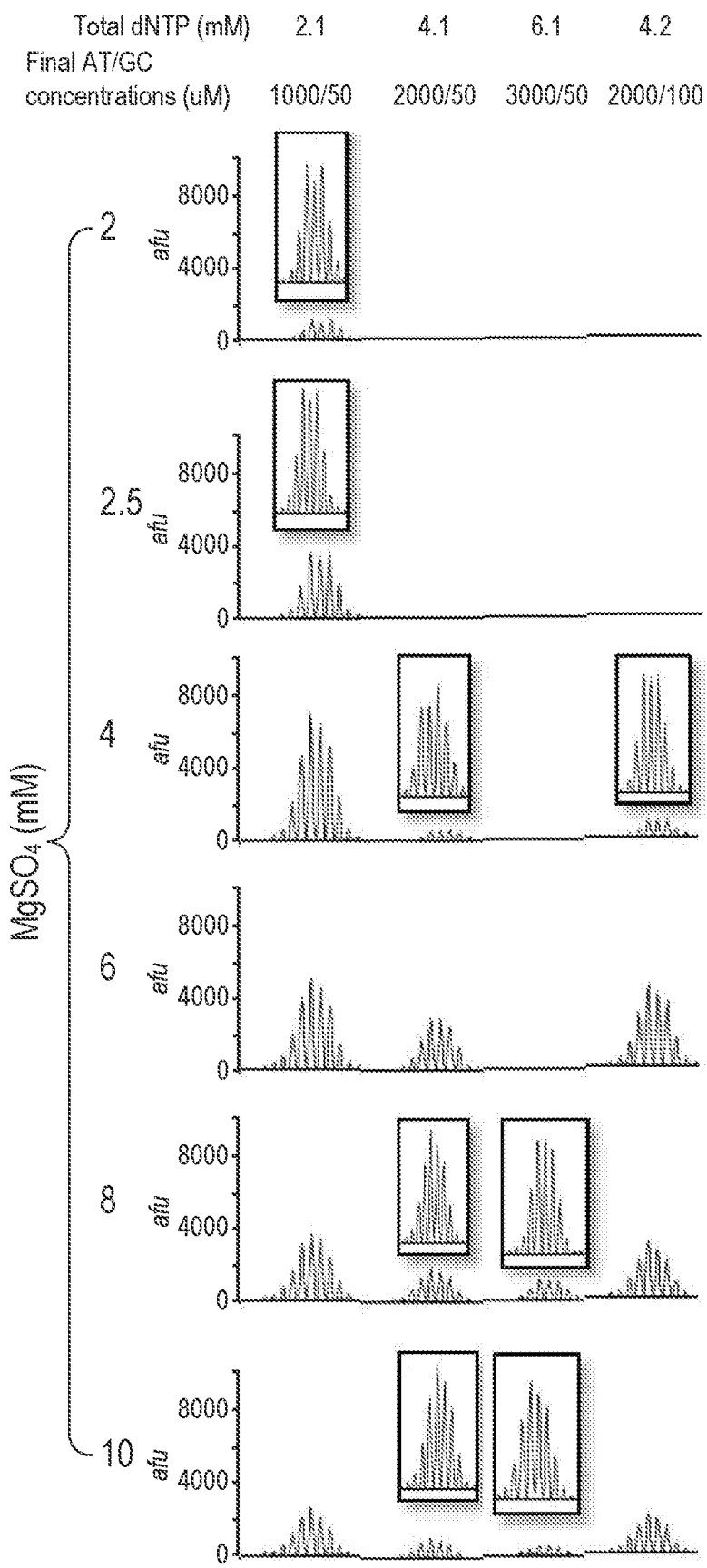
FIG. 5 depicts capillary electrophoresis results from an experiment testing the effects of $Mg^{2+}$ concentration, total dNTP concentration, and AT/GC biased ratios on polymerase slippage/stutter.

Results are depicted in FIGS. 4 and 5. FIG. 4 depicts results of varying Mg$^{2+}$ concentration and total dNTP concentration when AT/GC ratios were not biased. FIG. 4 confirmed that excess dNTP concentrations relative to Mg$^{2+}$ can inhibit DNA polymerase by sequestering magnesium ions.

FIG. 5 depicts results from varying Mg$^{2+}$ concentration and total dNTP concentration under different AT/GC ratio conditions. As shown in FIG. 5, the non-target 35T peak height was shorter than at least one of the 34T and 36T target peaks for multiple reaction conditions including: 1000/50 AT/GC, 2 mM Mg$^{2+}$; 1000/50 AT/GC, 2.5 mM Mg$^{2+}$; 1000/50 AT/GC, 4 mM Mg$^{2+}$; 2000/50 AT/GC, 4 mM Mg$^{2+}$; and 2000/100 AT/GC, 4 mM Mg$^{2+}$.

Example 3: Effect of Betaine and DMSO on Polymerase Slippage/Stuttering

To further evaluate reaction conditions for analysis of A- or T-rich homopolymeric regions, the effects of AT/GC ratio, betaine, and DMSO were assessed by conducting a series of reactions with varying AT/GC ratios (250/250, 250/25, 500/25, 500/50, and 1000/50), varying betaine amounts (0M, 1M), and varying DMSO concentrations (0%, 1%, 2%, and 4%). All reaction mixtures were admixed with 10 ng of RS1311 sample DNA (16T/36T). PCR was conducted for 35 cycles. CE analysis was performed as described in Example 1.

Figure 6:
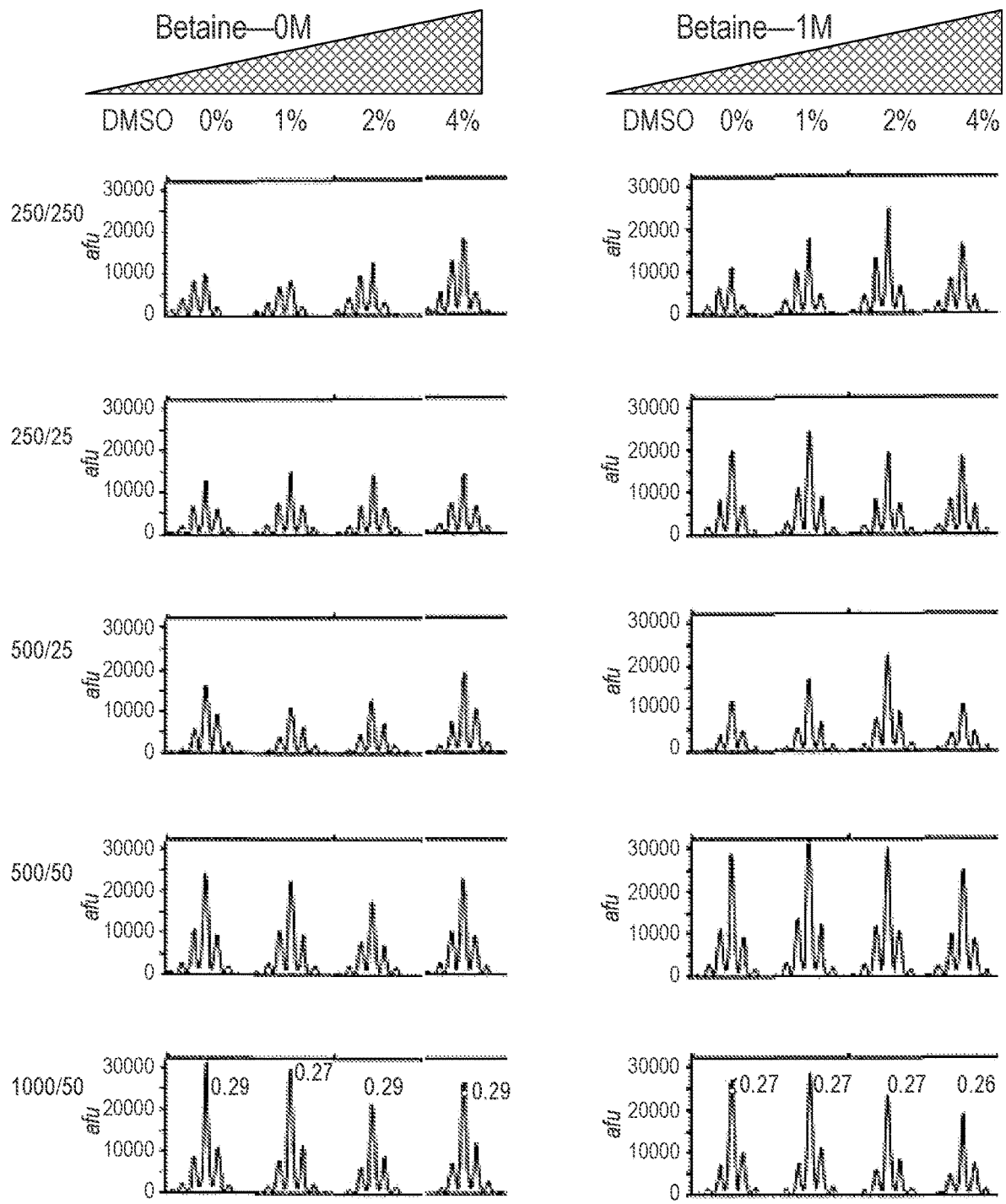
FIG. 6 depicts the effects of DMSO and betaine titration on polymerase slippage/stutter during amplification of a 16T TOMM40 polymorphism.
Figure 7:
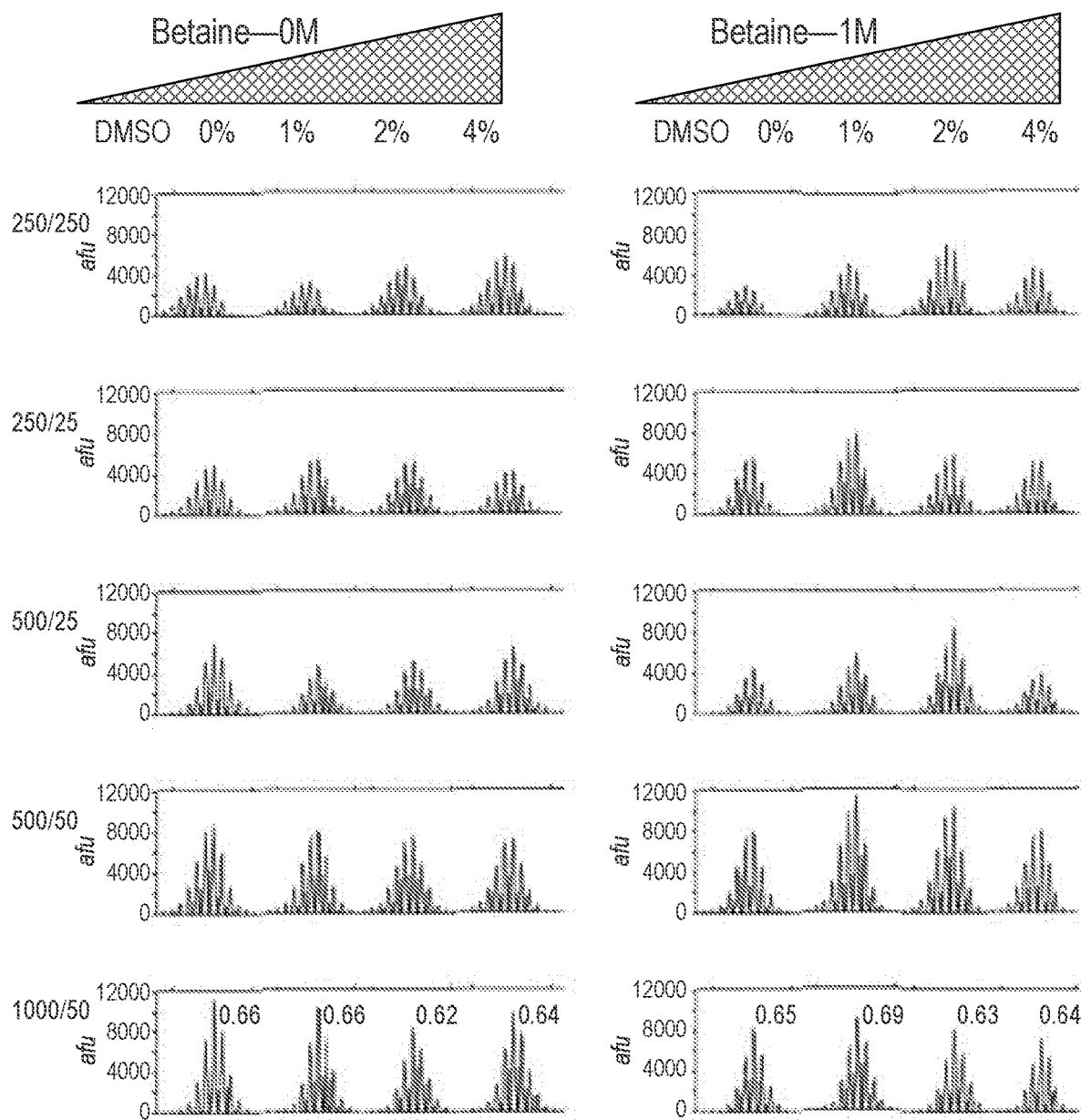
FIG. 7 depicts the effects of DMSO and betaine titration on polymerase slippage/stutter during amplification of a 36T TOMM40 polymorphism.

Results are depicted in FIGS. 6 and 7. FIG. 6 depicts the effects of DMSO and betaine titration in the vicinity of the 16T peak. Peak stutter generally decreased with biased AT/GC ratio conditions as compared to unbiased AT/GC ratio conditions, with the greatest decrease apparent at the 1000/50 ratio. The presence of 1M Betaine improved stutter, including in unbiased AT/GC ratio conditions.

FIG. 7 depicts the effects of DMSO and betaine titration in the vicinity of the 36T peak. Peak stutter generally decreased with biased AT/GC ratio conditions as compared to unbiased AT/GC ratio conditions, with the greatest decrease apparent at the 1000/50 ratio. 1M Betaine and 1% DMSO were also beneficial in reducing the stutter ratio (N−1/N).

Example 4: Effect of Reducing Number of PCR Cycles on Polymerase Stutter/Slippage The effect of lowering number of PCR cycles on polymerase slippage/stutter was assessed by varying PCR cycle numbers (25, 30, or 35 cycles). 10 ng of either RS1311 (16T/36T) or RS1319 (34T/36T) DNA samples were admixed with a PCR reaction mixture containing an AT/GC ratio of 1000/50, 1% DMSO, 1M Betaine, and 2.0 mM MgSO$_4$. PCR was run for 25, 30, or 35 cycles prior to CE analysis.

Figure 8:
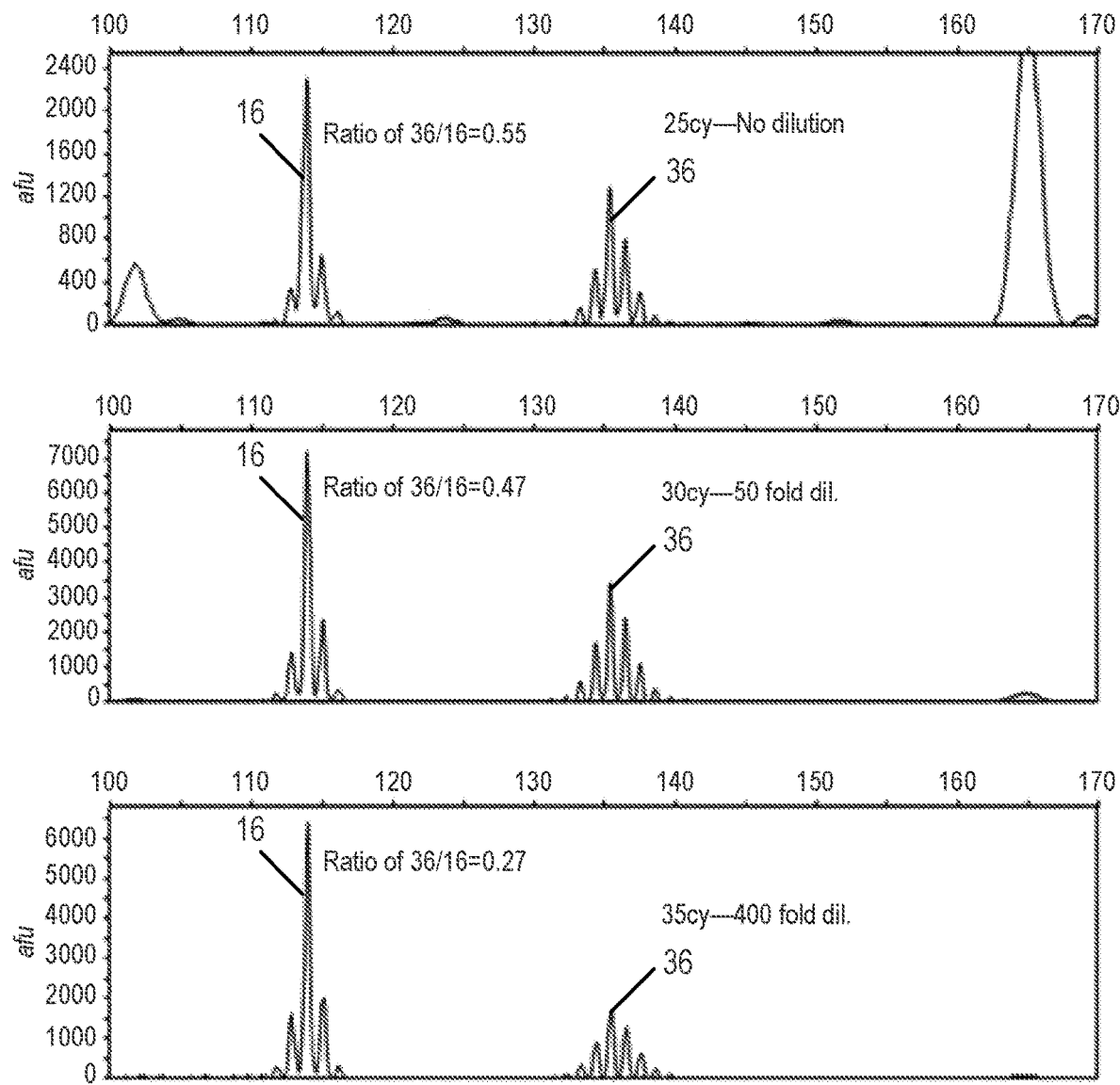
FIG. 8 depicts the effects of reduced PCR cycles on polymerase slippage/stutter during amplification of a 16T/36T TOMM40 polymorphism.
Figure 9:
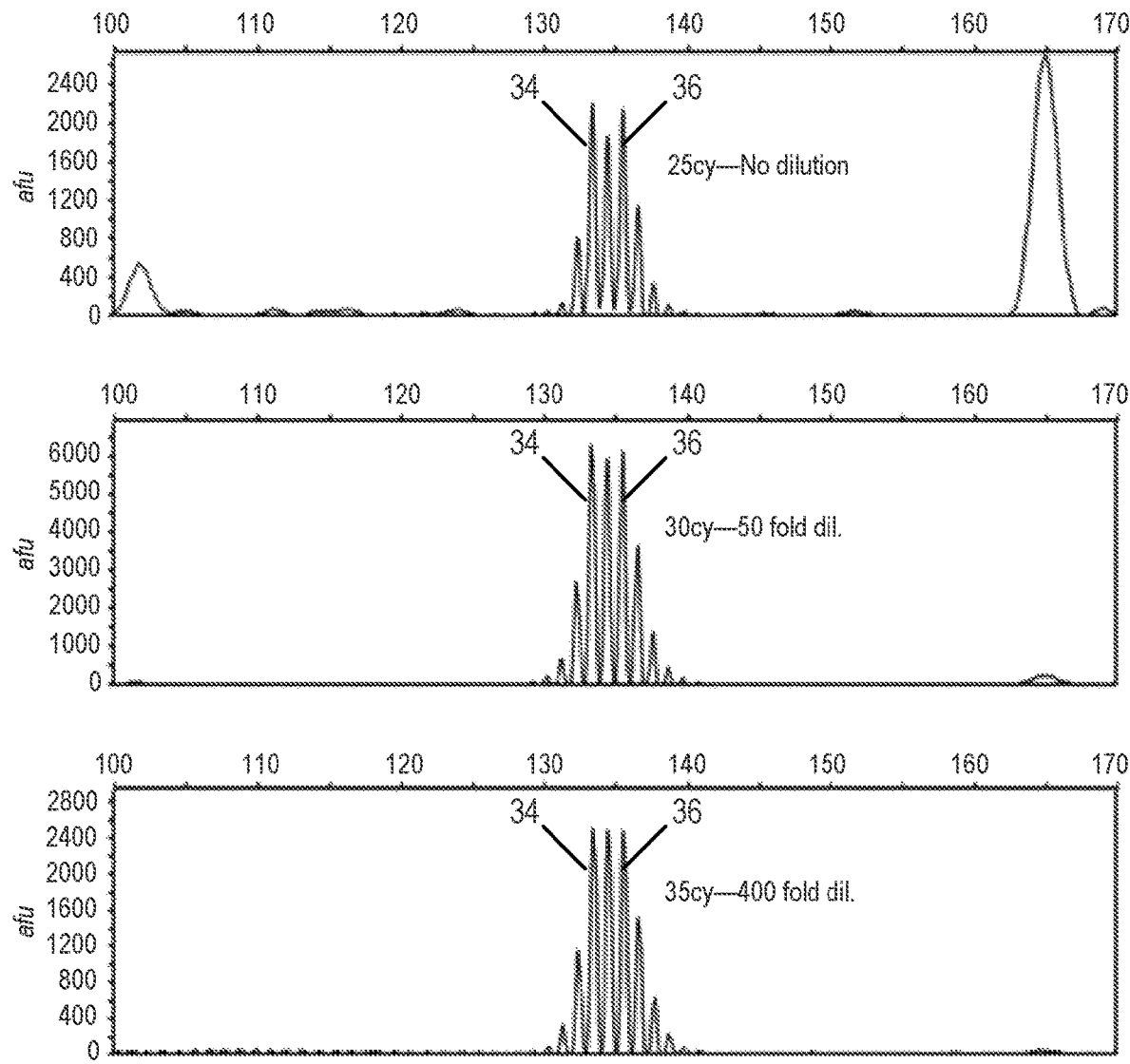
FIG. 9 depicts the effects of reduced PCR cycles on polymerase slippage/stutter during amplification of a 34T/36T TOMM40 polymorphism.

Results are depicted in FIGS. 8 and 9. FIG. 8 depicts the effect of PCR cycle numbers on 16T and 36T peak stutter. Because RS1311 samples are known to contain 16T and 36T alleles in a 1:1 ratio, 36/16 peak height ratios that approach 1 indicate reduced bias toward amplification of the shorter target allele. FIG. 8 shows that among the PCR cycle numbers tested, 25 cycles of PCR resulted in the 36/16 peak height ratio closest to 1.

FIG. 9 depicts the effect of PCR cycle numbers on 34T and 36T peak stutter. As shown in FIG. 9, the 35T non-target peak was shorter relative to the 34T and 36T peak heights with 25 or 30 PCR cycles as compared to 35 PCR cycles, with the shortest height demonstrated under 25 PCR cycle conditions.

Example 5: Combination of Biased dNTPs, Betaine, DMSO, and Lowered PCR Cycles Improved Polymerase Slippage/Stutter Heterozygous DNA samples described in Table 2 were provided. Samples were subjected to PCR reaction conditions as shown in Table 3.

TABLE 3

| Reaction conditions. | | |
|---|---|---|
|  | A | B |
| AT/GC concentration ratio (µM/µM) | 250/250 | 1000/50 |
| Mg++ | 2.5 mM MgCl$_2$ | 2.0 mM MgSO$_4$ |
| Betaine (M) | 0 | 1 |

TABLE 3-continued

| Reaction conditions. | | |
|---|---|---|
|  | A | B |
| DMSO (%) | 0 | 1 |
| PCR cycles | 35 | 27 |

Figure 10:
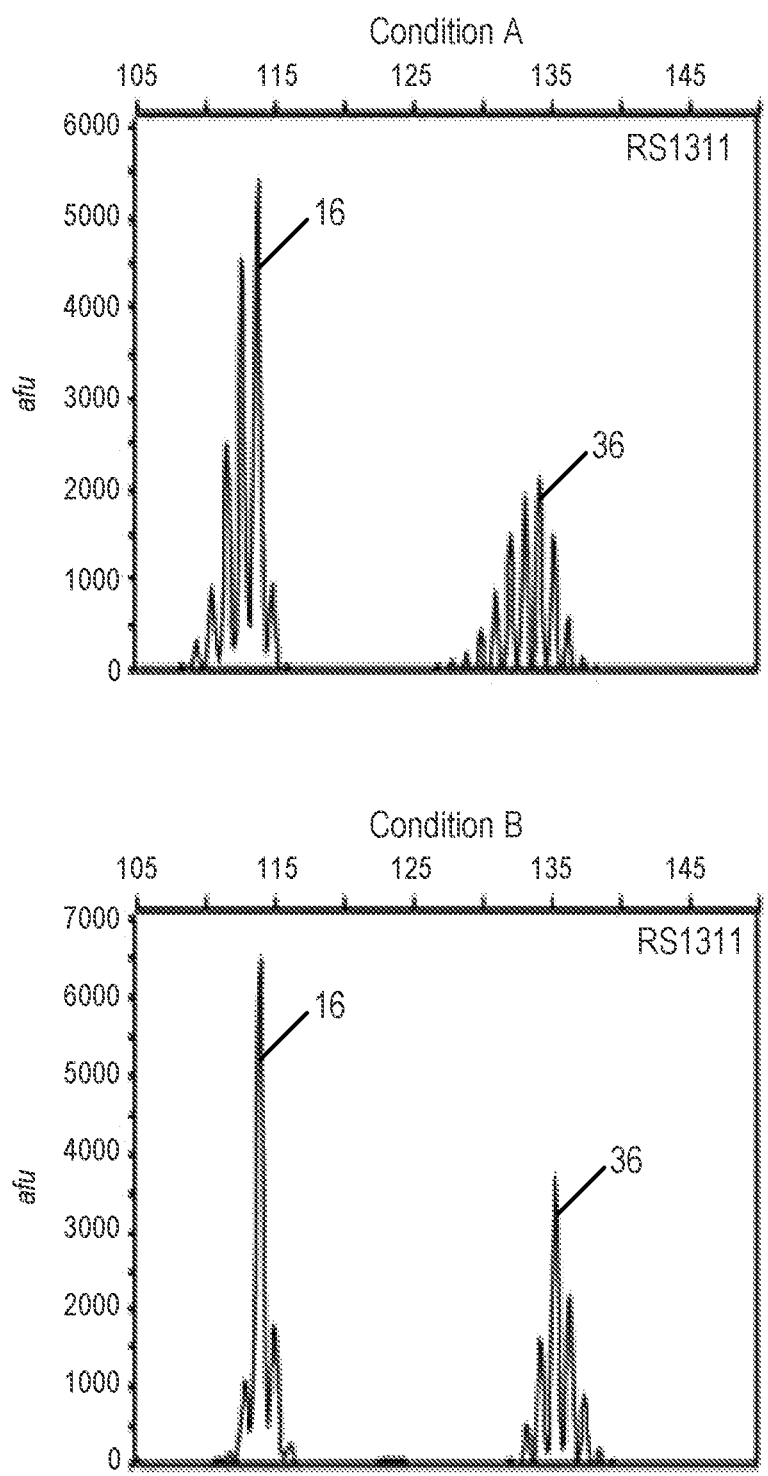
FIG. 10 depicts the effects of an increased AT/GC concentration ratio, lowered PCR cycle number (all in Condition B, relative to Condition A), 1M Betaine, and 1% DMSO on detection of short (16T) and very long (36T) TOMM40 polymorphic alleles.
Figure 11:
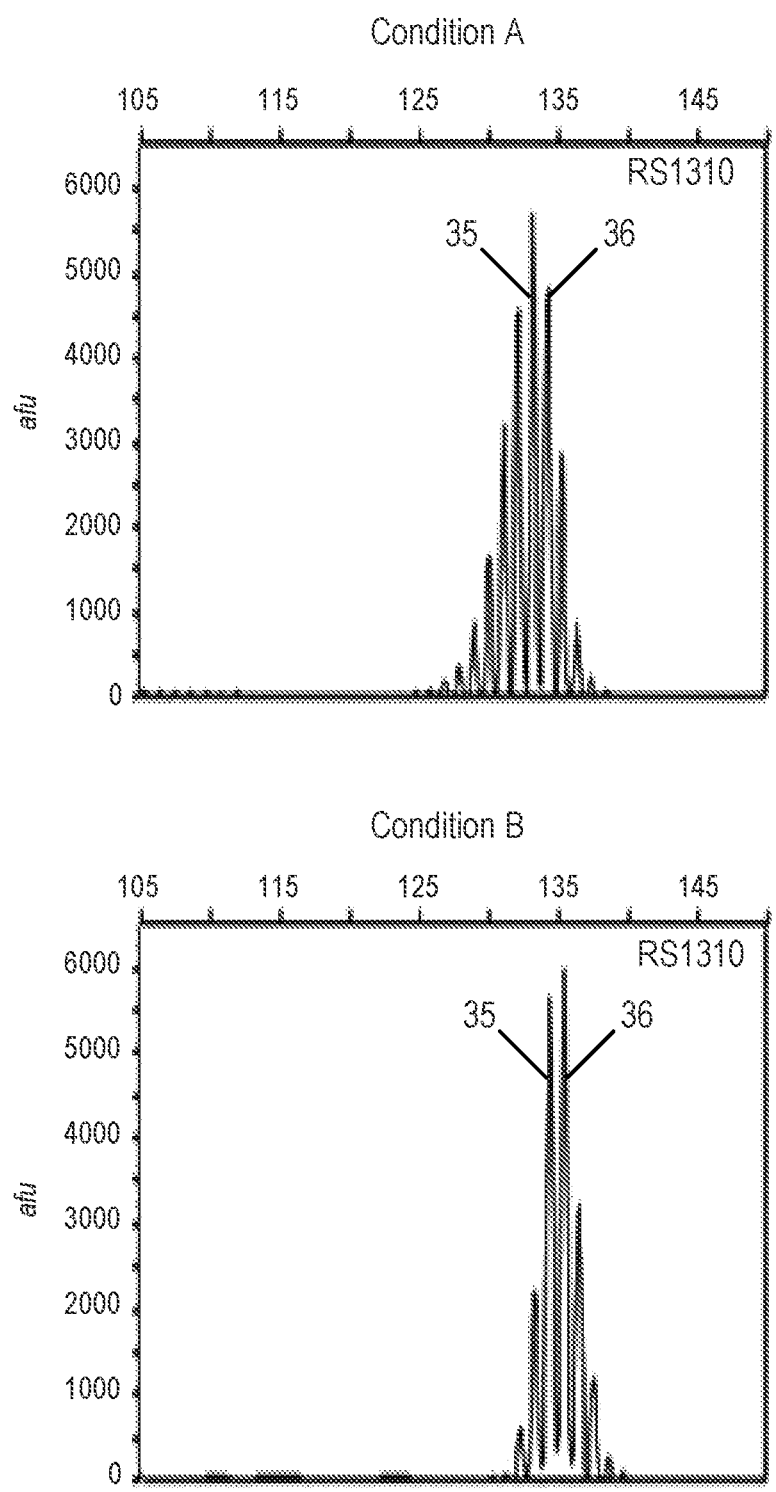
FIG. 11 depicts the effects of an increased AT/GC concentration ratio, lowered PCR cycle number, 1M Betaine, and 1% DMSO (all in Condition B, relative to Condition A) on detection of long polymorphic poly-T alleles that have adjacent lengths.
Figure 12:
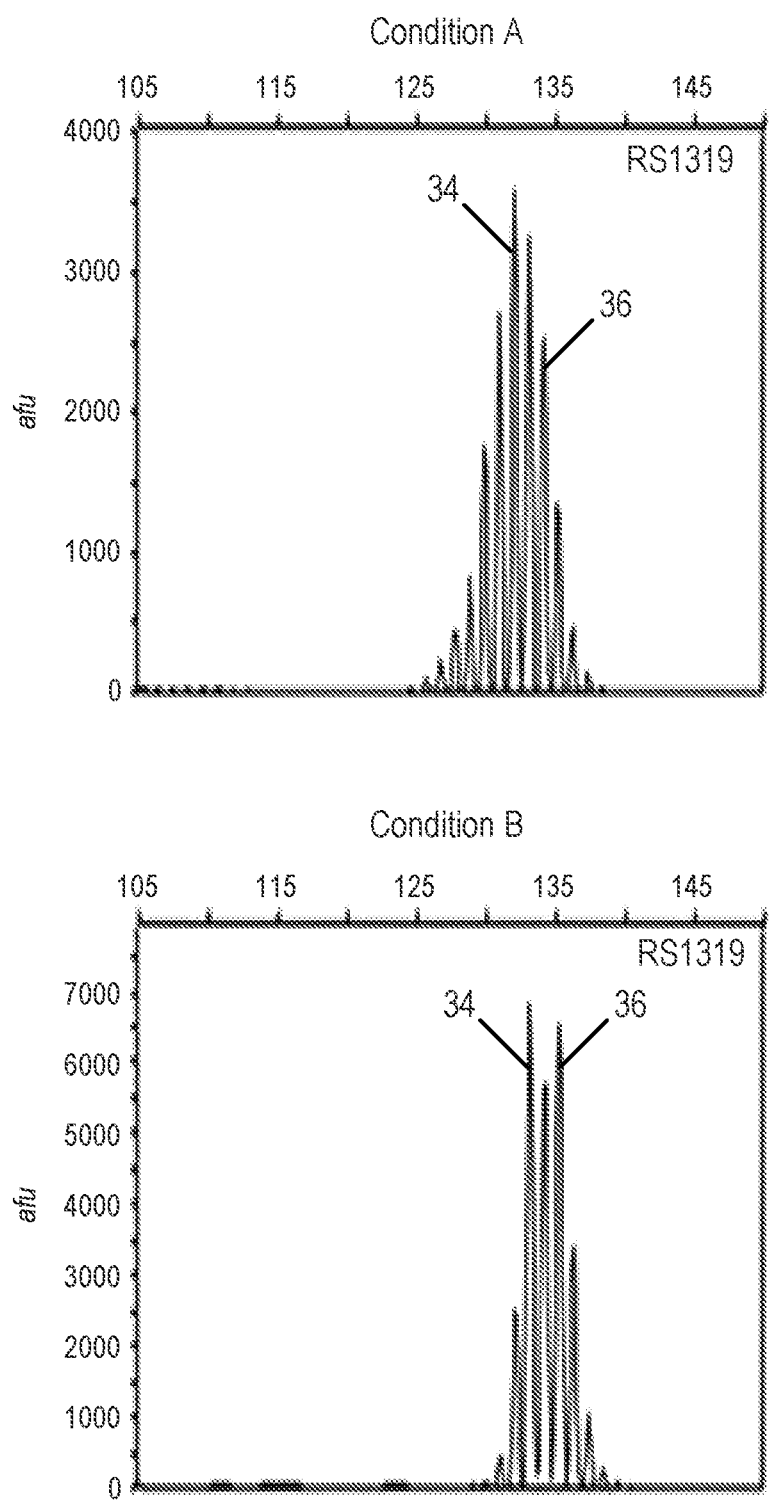
FIG. 12 depicts the effects of an increased AT/GC concentration ratio, lowered PCR cycle number, 1M Betaine, and 1% DMSO (all in Condition B, relative to Condition A) on detection of long polymorphic poly-T alleles that are separated in length by 1 nucleotide.

Results are depicted in FIGS. 10-12. FIG. 10 depicts results from the RS1311 (16T/36T) samples. As compared to the condition A, the increased AT/GC concentration ratio, lowered PCR cycle number, 1M Betaine, and 1% DMSO in condition B increased target/non-target peak height ratios for the 16T and 36T target peaks, and also increased the 36T/16T peak height ratio closer to 1.

FIG. 11 depicts results from the RS1310 (35T/36T) samples. As compared to condition A, the increased AT/GC concentration ratio, lowered PCR cycle number, 1M Betaine, and 1% DMSO in condition B increased target/non-target peak height ratios for the 35T and 36T target peaks, and reduced the number of non-target peaks.

FIG. 12 depicts results from the RS1319 samples. As compared to condition A, the increased AT/GC concentration ratio, lowered PCR cycle number, 1M Betaine, and 1% DMSO in condition B reduced the 35T non-target peak height relative to the 34T and 36T peak heights.

Example 6: Comparison of Conditions with and without DMSO and Betaine

Samples were subjected to PCR reaction conditions and analyzed by capillary electrophoresis as follows.

TABLE 4

| Reaction conditions. | | |
|---|---|---|
|  | B | C |
| AT/GC concentration ratio (µM/µM) | 1000/50 | 1000/50 |
| Mg++ | 2.0 mM MgSO$_4$ | 2.0 mM MgSO$_4$ |
| Betaine (M) | 1 | 0 |
| DMSO (%) | 1 | 0 |

For both conditions, MgSO$_4$ was supplied via Phoenix Hot Start Taq buffer. The PCR program was 95° C. 5 min; 10× (95° C., 30 s; 65° C. to 56° C. touchdown 1° C. per cycle, 30 s; 64° C., 30 s); 17× (95° C., 30 s; 55° C., 60 s).

Figure 13A:
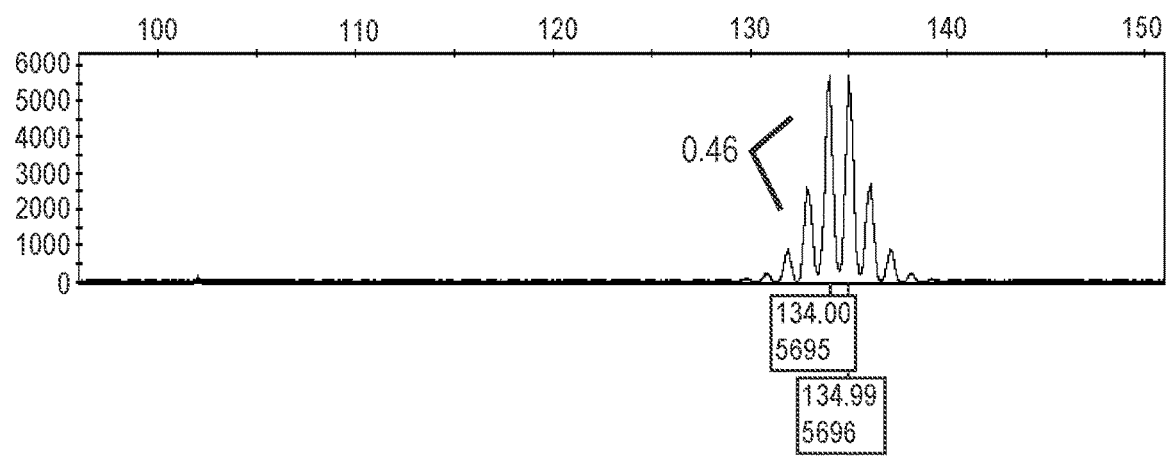
FIG. 13A shows products amplified from RS1310 (35T/36T) samples using condition C.

FIG. 13A shows products amplified from RS1310 (35T/36T) samples using condition C. The products were loaded at 2.5 kV for 5 seconds. The n−1/n ratio for the 34T and 35T peaks was 0.46.

Figure 13B:
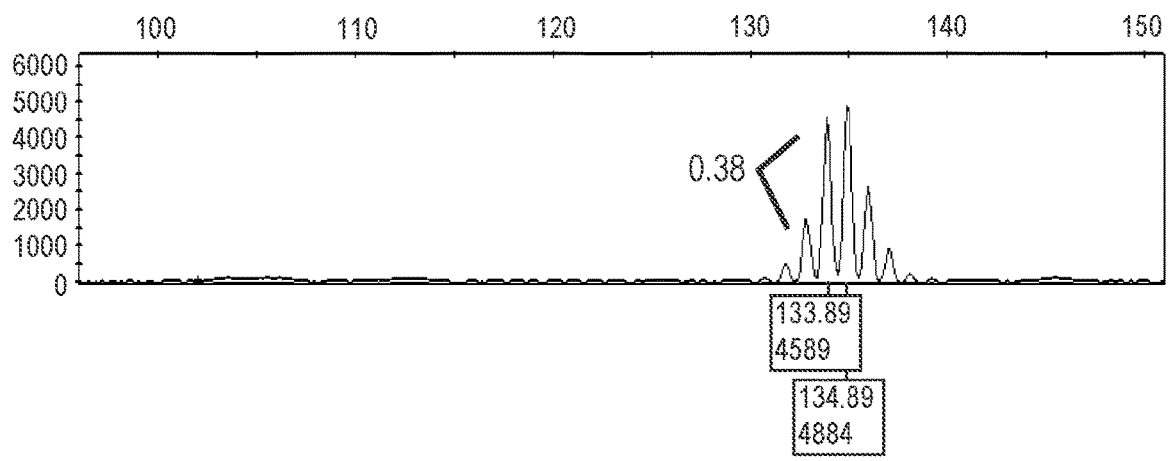
FIG. 13B shows products amplified from RS1310 (35T/36T) samples using condition B.

FIG. 13B shows products amplified from RS1310 (35T/36T) samples using condition B. The products were loaded at 2.5 kV for 20 seconds. The n−1/n ratio for the 34T and 35T peaks was 0.38.

Figure 14A:
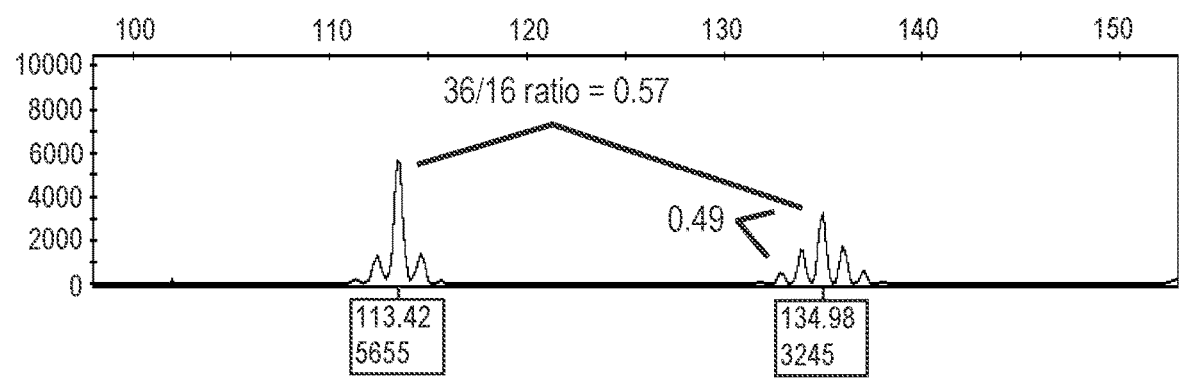
FIG. 14A shows products amplified from RS1311 (16T/36T) samples using condition C.

FIG. 14A shows products amplified from RS1311 (16T/36T) samples using condition C. The products were loaded at 2.5 kV for 5 seconds. The n−1/n ratio for the 35T and 36T peaks was 0.49. The peak height ratio of the 36T peak to the 16T peak was 0.57.

Figure 14B:
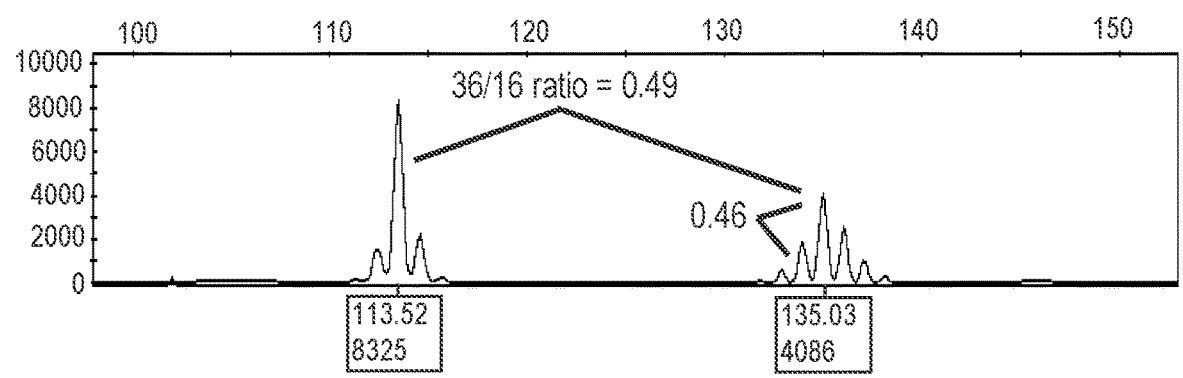
FIG. 14B shows products amplified from RS1311 (16T/36T) samples using condition B.

FIG. 14B shows products amplified from RS1311 (16T/36T) samples using condition B. The products were loaded at 2.5 kV for 20 seconds. The n−1/n ratio for the 35T and 36T peaks was 0.46. The peak height ratio of the 36T peak to the 16T peak was 0.49.

Figure 15A:
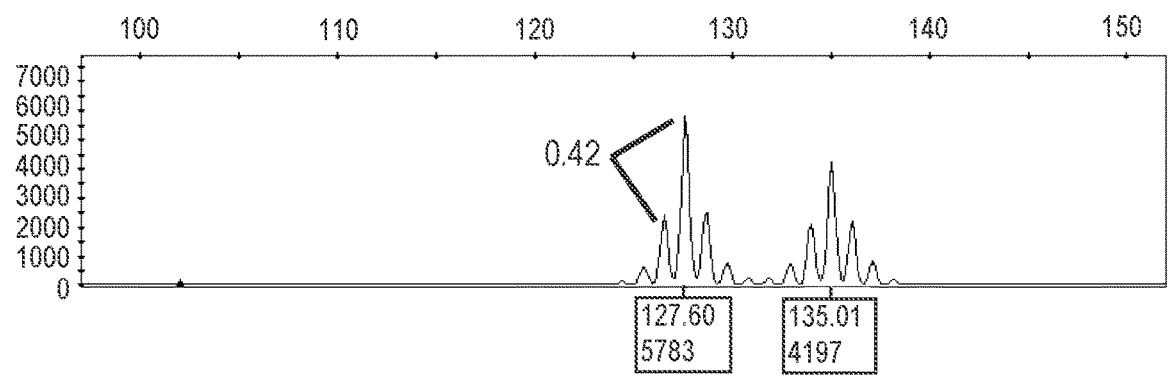
FIG. 15A shows products amplified from RS1317 (29T/36T) samples using condition C.

FIG. 15A shows products amplified from RS1317 (29T/36T) samples using condition C. The products were loaded at 2.5 kV for 5 seconds. The n−1/n ratio for the 28T and 29T peaks was 0.42.

Figure 15B:
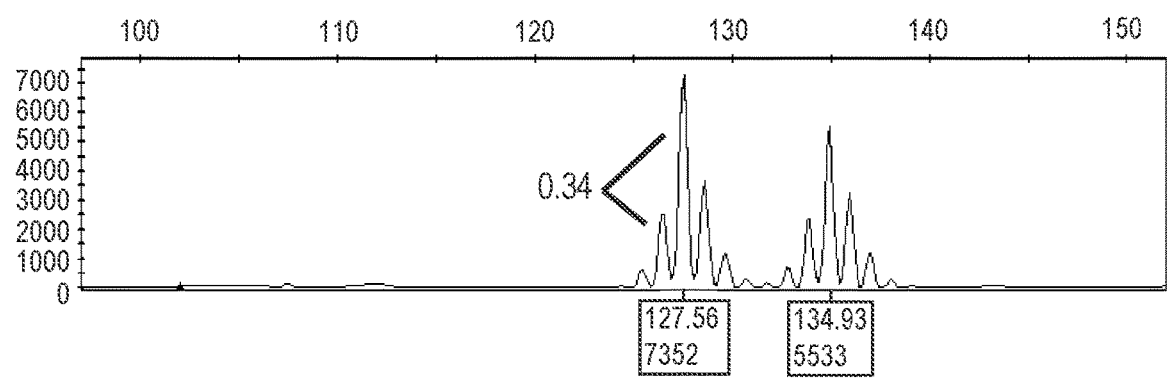
FIG. 15B shows products amplified from RS1317 (29T/36T) samples using condition B.

FIG. 15B shows products amplified from RS1317 (29T/ 36T) samples using condition B. The products were loaded at 2.5 kV for 20 seconds. The n−1/n ratio for the 28T and 29T peaks was 0.34.

Figure 16A:
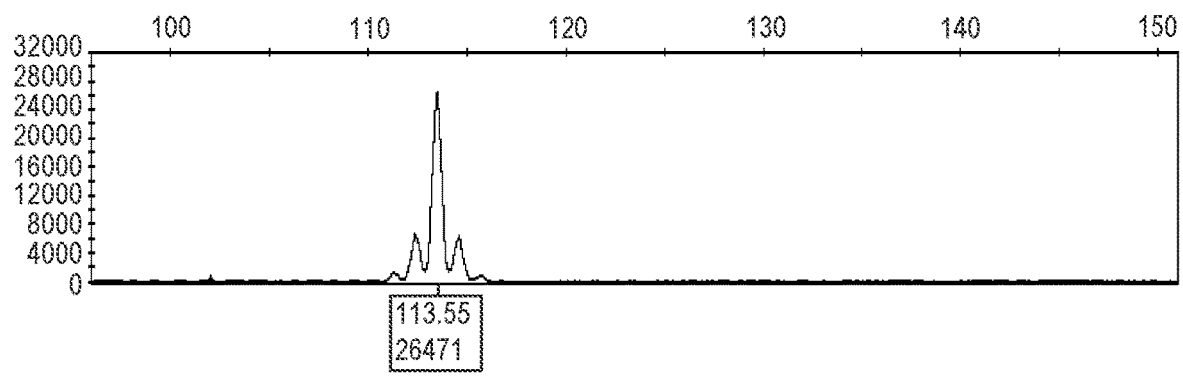
FIG. 16A shows products amplified from RS1318 (16T) samples using condition C.

FIG. 16A shows products amplified from RS1318 (16T) samples using condition C. The products were loaded at 2.5 kV for 5 seconds.

Figure 16B:
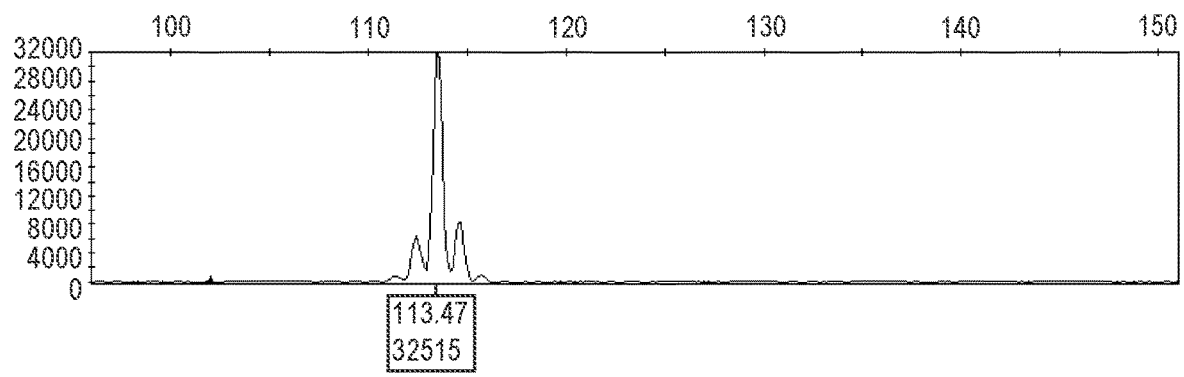
FIG. 16B shows products amplified from RS1318 (16T) samples using condition B.

FIG. 16B shows products amplified from RS1318 (16T) samples using condition B. The products were loaded at 2.5 kV for 20 seconds.

Figure 17A:
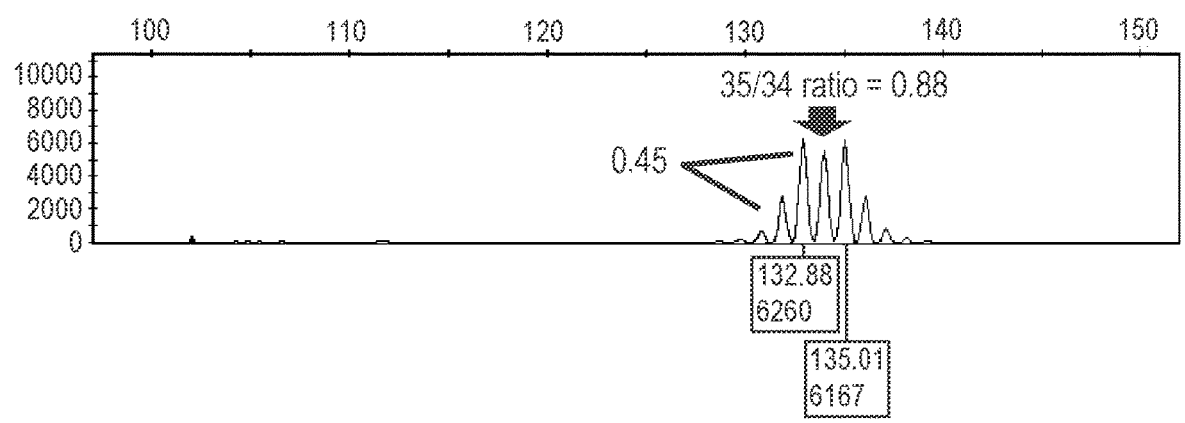
FIG. 17A shows products amplified from RS1319 (34T/36T) samples using condition C.

FIG. 17A shows products amplified from RS1319 (34T/ 36T) samples using condition C. The products were loaded at 2.5 kV for 5 seconds. The n−1/n ratio for the 33T and 34T peaks was 0.45. The peak height ratio of the 35T peak to the 34T peak was 0.88.

Figure 17B:
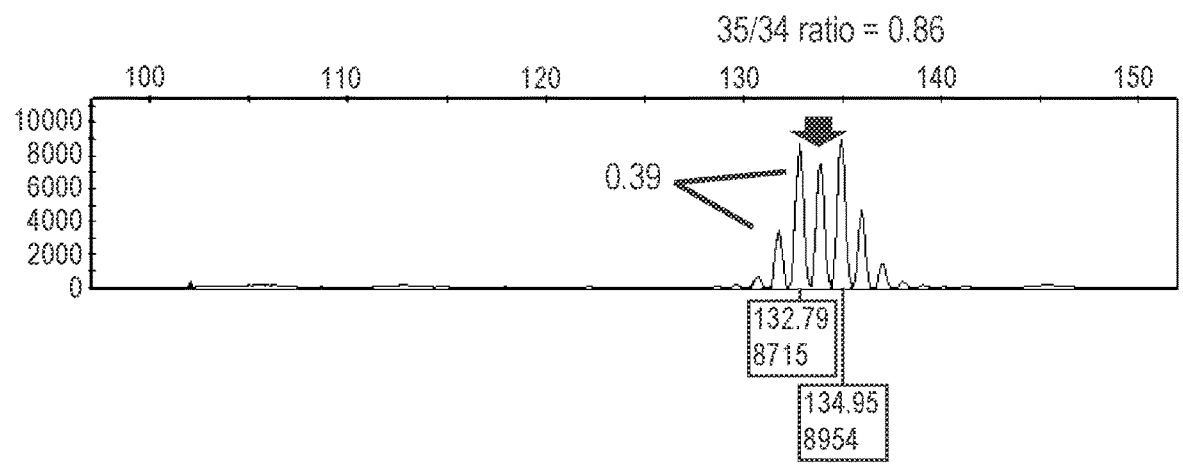
FIG. 17B shows products amplified from RS1319 (34T/36T) samples using condition B.

FIG. 17B shows products amplified from RS1319 (34T/ 36T) samples using condition B. The products were loaded at 2.5 kV for 20 seconds. The n−1/n ratio for the 33T and 34T peaks was 0.39. The peak height ratio of the 35T peak to the 34T peak was 0.86.

Figure 18A:
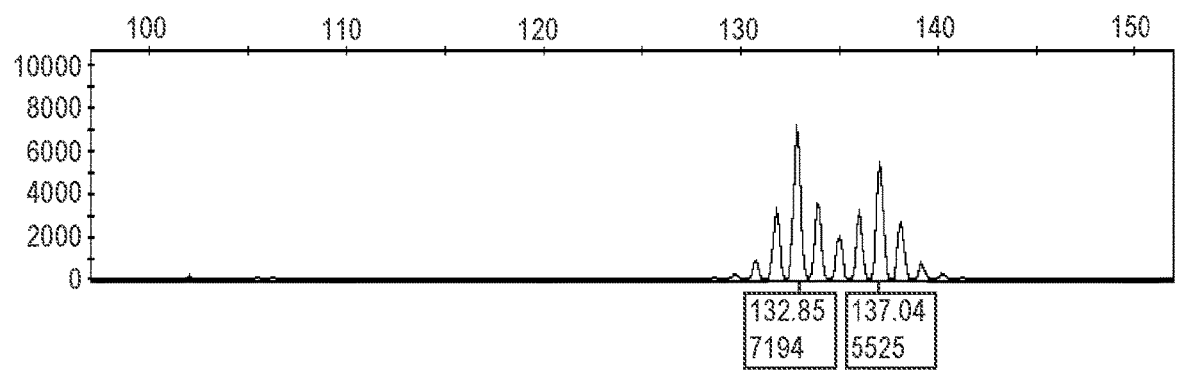
FIG. 18A shows products amplified from NA07541 (34T/38T) samples using condition C.

FIG. 18A shows products amplified from NA07541 (34T/ 38T) samples using condition C. The products were loaded at 2.5 kV for 5 seconds.

Figure 18B:
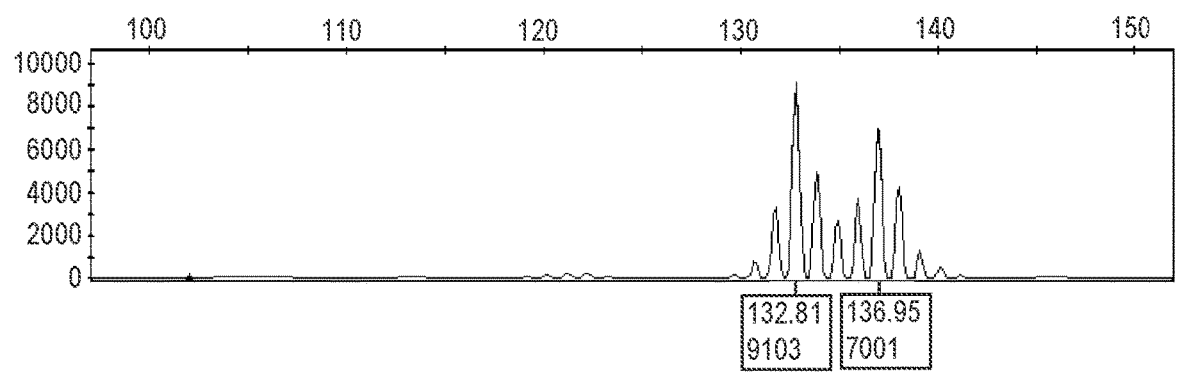
FIG. 18B shows products amplified from NA07541 (34T/38T) samples using condition B.

FIG. 18B shows products amplified from NA07541 (34T/ 38T) samples using condition B. The products were loaded at 2.5 kV for 20 seconds.

Figure 19A:
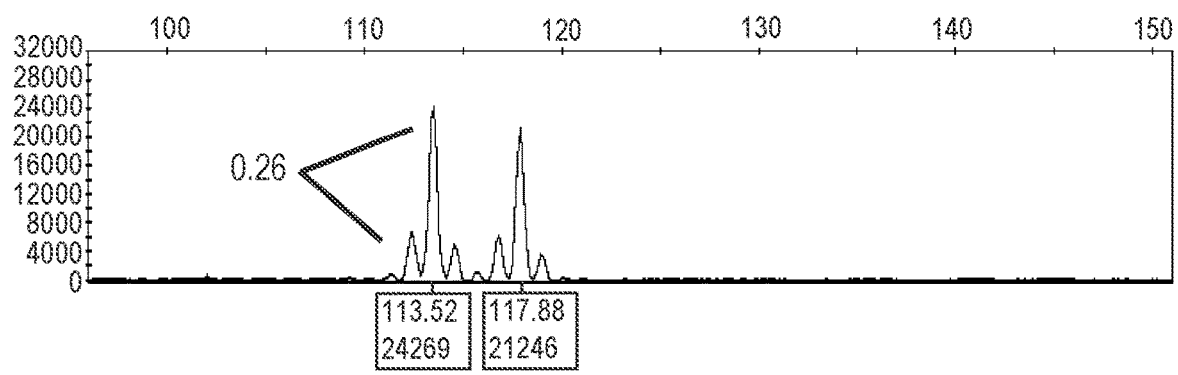
FIG. 19A shows products amplified from NA20243 (16T/20T) samples using condition C.

FIG. 19A shows products amplified from NA20243 (16T/ 20T) samples using condition C. The products were loaded at 2.5 kV for 5 seconds. The n−1/n ratio for the 15T and 16T peaks was 0.26.

Figure 19B:
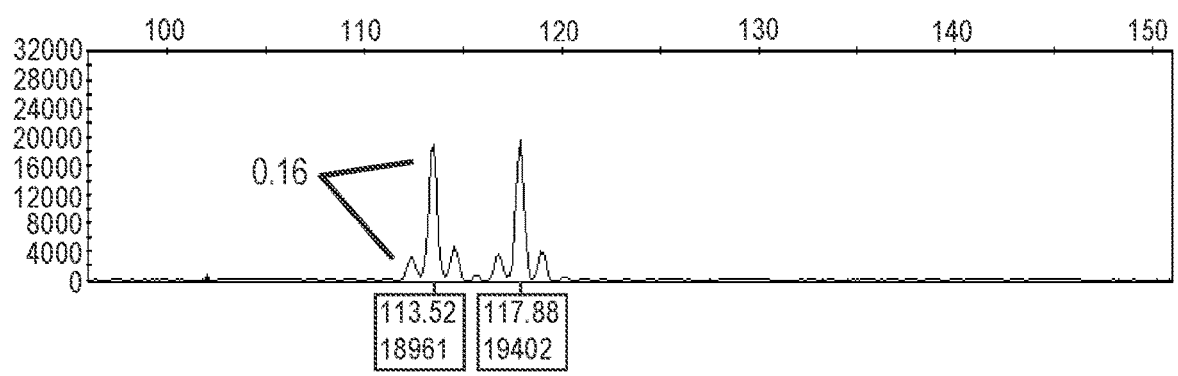
FIG. 19B shows products amplified from NA20243 (16T/20T) samples using condition B.

FIG. 19B shows products amplified from NA20243 (16T/ 20T) samples using condition B. The products were loaded at 2.5 kV for 20 seconds. The n−1/n ratio for the 15T and 16T peaks was 0.16.

The foregoing results generally show that condition C gave greater amplification efficiency, in that compared to condition B, four-fold lower load amounts (2.5 kV for 5 seconds) of products from condition C gave target peak heights similar to or moderately lower (less than 50% decrease) than peak heights for condition B products loaded at 2.5 kV for 20 seconds. The results also show that condition B permitted greater target vs. non-target peak discrimination in that, e.g., the n−1/n peak height ratios were generally lower. Furthermore, the results from condition C show that betaine and DMSO are not essential. Thus, conditions B and C illustrate how reaction conditions can be tailored to focus on amplification efficiency or target vs. non-target peak discrimination. High amplification efficiency can facilitate amplification procedures with reduced cycle numbers, and it was shown above that reduced cycle numbers can improve target vs. non-target peak discrimination.

Example 7: Amplification of 48T Homopolymeric Segment

Figure 20A:
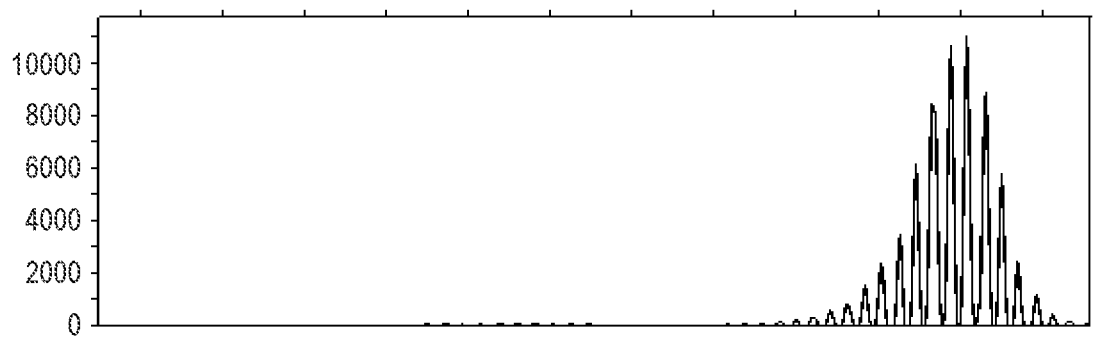
FIG. 20A shows products from a synthetic DNA template containing a 48T homopolymeric segment amplified using condition A.
Figure 20B:
FIG. 20B shows products from a synthetic DNA template containing a 48T homopolymeric segment amplified using condition B.

A sample of a synthetic DNA template containing a 48T homopolymeric segment was amplified using conditions A and B as in Example 5 and analyzed by capillary electrophoresis. Results from condition A are shown in FIG. 20A. Results from condition B are shown in FIG. 20B. The highest peak in FIG. 20B represents the 48T target peak. Non-target peaks containing 49T, 50T, 51T, 52T, and 53T segments were also detectable. Thus, homopolymeric segments of 48 nucleotides or more can be amplified and analyzed according to this disclosure.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. The listing of steps in a method in a particular order is not to be construed as an indication that the steps must be performed in that order, except where there is an explicit indication to the contrary or the result of one step is required for occurrence of another step.

What is claimed is:

1. A method of extending at least one nucleic acid template comprising a repeating A/T-rich segment, the method comprising performing a nucleic acid amplification reaction in an aqueous solution comprising the at least one nucleic acid template comprising target and non-target nucleic acid sequences;

at least one polymerase;

at least one primer;

$Mg^{2+}$; and

NTPs in an AT/GC ratio of 8 or higher;

to increase discrimination of target versus non-target nucleic acid sequences in resulting amplified products;

wherein the repeating A/T-rich segment is:

(i) a homopolymeric segment comprising at least 10 A residues, at least 10 T residues, or at least 10 U residues, wherein the at least 10 A, T, or U residues are consecutive or interrupted once by one to three nucleotides; or (ii) a segment comprising $(T_nA)_m$, $(AT_n)_m$, $(TA_n)_m$, or $(A_nT)_m$, wherein n is 2 or greater and m is such that the length of the repeating A/T-rich segment is 10 or more residues.

2. The method of claim 1, wherein the AT/GC ratio is a value ranging from about 10 to about 40.

3. The method of claim 1, wherein the NTPs comprise dNTPs or rNTPs, and are present in a total NTP concentration ranging from about 0.5 mM to about 5 mM.

4. The method of claim 1, wherein guanosine is present in a concentration ranging from about 10 µM to about 400 µM and cytidine is present in a concentration ranging from about 10 µM to about 400 µM.

5. The method of claim 1, wherein thymidine is present in a concentration ranging from about 700 µM to about 2000

μM and adenosine is present in a concentration ranging from about 700 μM to about 2000 μM.

6. The method of claim 1, wherein the Mg$^{2+}$ is present in a molarity ranging from about 80% to about 150% of the molarity of total NTPs.

7. The method of claim 1, wherein the magnesium is present in a concentration ranging from about 1.5 mM to about 3 mM.

8. The method of claim 1, wherein at least one nucleic acid template in the aqueous solution comprises a homopolymeric segment comprising 10 to 40 consecutive A residues or 10 to 40 consecutive T residues.

9. The method of claim 1, wherein at least one nucleic acid template in the aqueous solution comprises a homopolymeric segment of at least 10 consecutive T residues.

10. The method of claim 1, wherein at least one nucleic acid template in the aqueous solution comprises a segment comprising $(T_nA)_m$, $(AT_n)_m$, $(TA_n)_m$, or $(A_nT)_m$, wherein n is 2 or greater and m is such that the length of the repeating A/T-rich segment is about 10 or more residues.

11. The method of claim 10, wherein n is a value ranging from 3 to 10.

12. The method of claim 10, wherein m is a value ranging from 2 to 20.

13. The method of claim 10, wherein the length of the repeating A/T-rich segment ranges from about 10 to about 60 residues.

14. The method of claim 1, wherein the aqueous solution comprises at least two primers, wherein at least one primer comprises a 3'-terminal sequence that specifically hybridizes to two or more consecutive A residues or to two or more consecutive T residues.

15. The method of claim 14, wherein the at least one primer comprises a 3'-terminal sequence comprising 4 to 9 consecutive A residues or 4 to 9 consecutive T residues.

16. The method of claim 1, wherein the aqueous solution comprises at least two primers, wherein at least one primer comprises a covalently attached label.

17. The method of claim 1, wherein the amplification reaction is PCR.

18. The method of claim 17, wherein the PCR comprises no more than 35 cycles.

19. The method of claim 17, wherein the PCR comprises an annealing step at a temperature ranging from about 52° C. to about 58° C.

20. The method of claim 17, wherein the PCR comprises a first cycle comprising an annealing step at a first temperature and a second cycle after the first cycle, the second cycle comprising an annealing step at a second temperature, wherein the second temperature is lower than the first temperature.

21. The method of claim 1, wherein the at least one polymerase comprises a hot-start DNA polymerase.

22. The method of claim 1, wherein the method further comprises distinguishing a first sample comprising a first template with a homopolymeric segment of length (n+1) and a second template with a homopolymeric segment of length (n−1) from a sample comprising a template with a homopolymeric segment of length (n), wherein n is greater than 20 and less than 40.

23. The method of claim 1, wherein at least one nucleic acid template in the aqueous solution comprises a homopolymeric segment comprising at least 12 consecutive A residues or at least 12 consecutive T residues.

24. The method of claim 1, wherein at least one nucleic acid template in the aqueous solution comprises a homopolymeric segment in a genetic locus associated with late-onset Alzheimer's disease.

25. The method of claim 1, wherein at least one nucleic acid template in the aqueous solution comprises a subset of TOMM40 sequence comprising a homopolymeric segment of at least 10 consecutive T residues.

26. The method of claim 1, wherein the aqueous solution comprises at least two primers, wherein a first primer hybridizes upstream of the rs10524523 variable length polymorphism of the TOMM40 gene and a second primer hybridizes downstream of the rs10524523 variable length polymorphism of the TOMM40 gene.

27. A method of amplifying at least one DNA template comprising a homopolymeric segment, the method comprising performing a DNA amplification reaction in an aqueous solution comprising the at least one DNA template; at least one hot-start DNA polymerase; at least two primers; Mg$^{2+}$ at a concentration ranging from 1.5 mM to 3 mM; dNTPs in an AT/GC ratio of 8 or higher; and a total dNTP concentration ranging from 1500 μM to 2500 μM,
wherein the homopolymeric segment comprises at least 12 consecutive A residues or at least 12 consecutive T residues.

28. The method of claim 1, wherein the method comprises less than 35 amplification cycles.

29. The method of claim 1, wherein the AT/GC molar ratio is about 15 to about 40.

30. The method of claim 1, wherein the method comprises about 20 to about 35 amplification cycles and the AT/GC molar ratio is about 15 to about 60.

31. The method of claim 1, wherein the method comprises about 25 to about 35 amplification cycles, the AT/GC molar ratio is about 20 to about 40, and the Mg$^{2+}$ is at a concentration of about 2 mM to about 3 mM.

32. The method of claim 1, wherein the aqueous solution comprises betaine.

33. The method of claim 1, wherein the aqueous solution comprises DMSO.

34. The method of claim 1, wherein the aqueous solution comprises about 0.2 mM to about 2 mM betaine, about 0.4 mM to about 4 mM DMSO, or combinations thereof.

35. The method of claim 1, wherein the Mg$^{2+}$ is at a concentration of about 2 mM to about 11 mM.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ccaaagcatt gggattactg gc                                             22

<210> SEQ ID NO 2
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
gattgcttga gcctaggcat tc                                             22
```

```
<210> SEQ ID NO 3
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aataataata at                                                          12

<210> SEQ ID NO 4
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
aataaataat                                                             10

<210> SEQ ID NO 5
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 5
aaataaaaat                                                             10

<210> SEQ ID NO 6
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 6
aataaaaaat                                                             10
```